United States Patent [19]
Leung et al.

[11] Patent Number: 5,859,222
[45] Date of Patent: Jan. 12, 1999

[54] HUMAN PHOSPHATIDYLCHOLINE PHOSPHOLIPASE D

[75] Inventors: David W. Leung, Mercer Island; Christopher K. Tompkins, Bothell, both of Wash.

[73] Assignee: Cell Therapeutics, Inc., Seattle, Wash.

[21] Appl. No.: 768,147

[22] Filed: Dec. 17, 1996

Related U.S. Application Data

[60] Provisional application No. 60/008,768 Dec. 15, 1995.
[51] Int. Cl.$^6$ .............................. C07H 21/04; C12N 9/20; C12Q 1/00; C07K 1/00
[52] U.S. Cl. ...................... 536/23.2; 536/23.5; 435/69.1; 435/198; 435/252.3; 435/320.1; 435/4; 530/350
[58] Field of Search .................................. 536/23.1, 23.2, 536/23.5; 435/69.1, 252.3, 320.1, 198, 4; 530/350

[56] References Cited

U.S. PATENT DOCUMENTS 5,342,764  8/1994  Johnson et al. ......................... 435/69.1

FOREIGN PATENT DOCUMENTS

WO 98/10076  3/1998  WIPO.

OTHER PUBLICATIONS

Lopez et al., National Center for Biotechnology Info., Accession No. AF035483, Jun. 27, 1998, "Cloning and Initial Characterization of a Human Phospholipase D2: ARF Regulates hPLD2: ARF Regulates hPLD2", Jun. 27, 1998.

SAQIB, K.M. et al., National Center for Biotechnology Info., Accession No. AF038441, "Cloning and Expression of the cDNA for human phospholipase D2; differential expression of human phospholipase D1 and 2", Jan. 16, 1998.

SAQIB, K.M. et al., National Center for Biotechnology Info., Accession No. AF038440, "Cloning and Expression of the cDNA for human phospholipase D2; differential expression of human phospholipase D1 and 2", Jan. 16, 1998.

Yoshimura, S. et al., National Center for Biotechnology Info., Accession No. AB003172 D85729, "Differential mRNA expression of phospholipase D (PLD) isozymes during cAMP–induced differentiation in c6 glioma cells", Dec. 26, 1997.

Steed, P.M. et al., National Center for Biotechnology Info., Accession No. AF033850, "Phospholipase D: molecular cloning and characterization of human PLD2 and the analysis of PLD isoform splice variants", Nov. 27, 1997.

Colley, W.C. et al., National Center for Biotechnology Info., Accession No. U87557, "Phospholipase D2, a distinct phospholipase D isoform with novel regulatory properties that provokes cytoskeletal reorganization", May 14, 1997.

Barbas et al., *Methods: A Comparion to Methods in Enzymology*, vol. 2, No. 2, pp. 119–124, "Combinatorial Immunoglobulin Libraries on the Surface of Phage (Phabs): Rapid Selection of Antigen–Specific Fabs", 1991.

Brown et al., *Journal of Biological Chemistry*, vol. 270, No. 25, pp. 14935–14943, "Partial Purification and Characterization of Arf–sensitive Phospholipase D from Porcine Brain", 1995.

Ella et al., *Analytical Biochemistry*, vol. 218, pp. 136–142, "A Fluorescent Assay for Agonist–Activated Phospolipase D in Mammalian Cell Extracts", 1994.

Ella et al., *Biochem. J.*, vol. 314, pp. 15–19, "Characterization of *Saccharomyces cerevisiae* deficient in expression of phosholipase D", 1996.

Exton, *Biochimica et Biophysica Acta*, vol. 1212, pp. 26–42, "Phosphatidylcholine breakdown and signal transduction", 1994.

Hammond et al., *Journal of Biological Chemistry*, vol. 270, No. 50, pp. 29640–29643, "Human ADP–ribosylation Factor–activated Phospholipase D Defines a New and Highly Conserved Gene Family", 1995.

Honigberg et al., *Genetics*, vol. 130, pp. 703–716, "Commitment to Meiosis in *Saccharomyces cerevisiae*: Involvement of the SPO14 Gene", 1992.

Kiss, *Chemistry and Physics of Lipids*, vol. 80, pp. 81–102, "Regulation of phospholipase D by protein kinase C", 1996.

Kozak, *Critical Reviews in Biochemistry and Molecular Biology*, vol. 27(4,5), pp. 385–402, "A Consideration of Alternative Models for the Initiation of Translation in Eukaryotes", 1992.

LaVallie et al., *Journal of Biological Chemistry*, vol. 268, No. 31, pp. 23311–23317, "Cloning and Functional Expression of a cDNA Encoding the Catalytic Subunit of Bovine Enterokinase", 1993.

Leung et al., *Proc. Natl. Acad. Sci.*, vol. 92, pp. 4813–4817, "CT–2576, an inhibitor of phospholipid signaling, suppresses constitutive and induced expression of human immunodeficiency virus", 1995.

Liscovitch et al., *Chemistry and Physics of Lipids*, vol. 80, pp. 37–44, "Enzymology of mammalian phospholipases D: in vitro studies", 1996.

Okamura et al., *Journal of Biological Chemistry*, vol. 269, No. 49, pp. 31207–31213, "Purification and Characterization of Phosphatidylcholine Phospholipase D from Pig Lung", 1994.

Rice et al., *Proc. Natl. Acad. Sci. USA*, vol. 91, pp. 3857–3861, "Protection from endotoxic shock in mice by pharmacologic inhibition of phosphatidic acid", 1994.

Rose et al., *Proc. Natl. Acad. Sci. USA*, vol. 92, pp. 12151–12155, "Phospholipase D signaling is essential for meiosis", 1995.

(List continued on next page.)

*Primary Examiner*—Robert A. Wax
*Assistant Examiner*—Tekchand Saidha
*Attorney, Agent, or Firm*—Cell Therapeutics, Inc.; Stephen Faciszewski, Esq.

[57] ABSTRACT

Disclosed are human cDNA and polypeptides sequences having phosphatidylcholine phospholipase D (PCPLD).

1 Claim, 2 Drawing Sheets

OTHER PUBLICATIONS

Saito et al., *Archives of Biochemistry and Biophysics,* vol. 169, pp. 318–323, "Phosphatidohydrolase Activity in a Solubilized Preparation From Rat Brain Particulate Fraction", 1975.

Singer et al., *Exp. Opin. Invest. Drugs,* vol. 3, No. 6, pp. 631–643, "Inhibitors of intracellular phosphatidic acid production: novel therapeutics with broad clinical applications", 1994.

Ueki et al., *Plant Cell Physiol.,* vol. 36, No. 5, pp. 903–914, "Purification and Characterization of Phospholipase D (PLD) from Rice (Oryza sativa L.) and Cloning of cDNA for PLD from Rice and Maize (*Zea mays* L.)", 1995.

Uetsuki et al., *Journal of Biological Chemistry,* vol. 264, No. 10, pp. 5791–5798, "Isolation and Characterization of the Human Chromosomal Gene for Polypeptide Chain Elongation Factor–1$\alpha$", 1989.

Vinggaard et al., *Biochimica et Biophysica Acta,* vol. 1258, pp. 169–176, "Characterization and partial purification of phospholipase D from human placenta", 1995.

Wang et al., *Journal of Biological Chemistry,* vol. 269, No. 32, pp. 20312–20317, "Cloning and Expression of Phosphatidylcholine–hydrolyzing Phospholipase D from *Ricinus communis* L.", 1994.

Winter et al., *Annu. Rev. Immunol.,* vol. 12, pp. 433–455, "Making Antibodies By Phage Display Technology", 1994.

SEQUENCE LISTING ( 1 ) GENERAL INFORMATION:

( i i i ) NUMBER OF SEQUENCES:14

( 2 ) INFORMATION FOR SEQ ID NO:1:

( i ) SEQUENCE CHARACTERISTICS:
        ( A ) LENGTH: 3425
        ( B ) TYPE: nucleic acid
        ( C ) STRANDEDNESS: single stranded
        ( D ) TOPOLOGY: linear ( i i ) MOLECULE TYPE: cDNA to mRNA ( i i i ) HYPOTHETICAL: no ( i v ) ANTI-SENSE: no ( v ) FRAGMENT TYPE:

( v i ) ORIGINAL SOURCE:
        ( A ) ORGANISM: homo sapien
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: hPCPLD
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:1:

( x i ) SEQUENCE DESCRIPTION:SEQ ID NO:1:

```
TGCAGCTCCG GTCTGCTCTC TTGGCTCGGG AACCCCCGCG GGCGCTGGCT           50

CCGTCTGCCA GGG                                                   63

ATG ACG GCG ACC CCT GAG AGC CTC TTC CCC ACT GGG GAC GAA  105
        Met Thr Ala Thr Pro Glu Ser Leu Phe Pro Thr Gly Asp Glu
                         5                  10

CTG GAC TCC AGC CAG CTC CAG ATG GAG TCC GAT GAG GTG GAC ACC      150
Leu Asp Ser Ser Gln Leu Gln Met Glu Ser Asp Glu Val Asp Thr
 15              20                  25

CTG AAG GAG GGA GAG GAC CCA GCC GAC CGG ATG CAC CCG TTT CTG      195
Leu Lys Glu Gly Glu Asp Pro Ala Asp Arg Met His Pro Phe Leu
 30              35                  40

GCC ATC TAT GAG CTT CAG TCT CTG AAA GTG CAC CCC TTG GTG TTC      240
Ala Ile Tyr Glu Leu Gln Ser Leu Lys Val His Pro Leu Val Phe
 45              50                  55

GCA CCT GGG GTC CCT GTC ACA GCC CAG GTG GTG GGC ACC GAA AGA      285
Ala Pro Gly Val Pro Val Thr Ala Gln Val Val Gly Thr Glu Arg
 60              65                  70

TAT ACC AGC GGA TCC AAG GTG GGA ACC TGC ACT CTG TAT TCT GTC      330
Tyr Thr Ser Gly Ser Lys Val Gly Thr Cys Thr Leu Tyr Ser Val
 75              80                  85

CGC TTG ACT CAC GGC GAC TTT TCC TGG ACA ACC AAG AAG AAA TAC      375
Arg Leu Thr His Gly Asp Phe Ser Trp Thr Thr Lys Lys Lys Tyr
 90              95                  100

CGT CAT TTT CAG GAG CTG CAT CGG GAC CTC CTG AGA CAC AAA GTC      420
Arg His Phe Gln Glu Leu His Arg Asp Leu Leu Arg His Lys Val
 105             110                 115

TTG ATG AGT CTG CTC CCT CTG GCT CGA TTT GCC GTT GCC TAT TCT      465
Leu Met Ser Leu Leu Pro Leu Ala Arg Phe Ala Val Ala Tyr Ser
 120             125                 130

CCA GCC CGA GAT GCA GGC AAC AGA GAG ATG CCC TCT CTA CCC CGG      510
Pro Ala Arg Asp Ala Gly Asn Arg Glu Met Pro Ser Leu Pro Arg
 135             140                 145

GCA GGT CCT GAG GGC TCC ACC AGA CAT GCA GCC AGC AAA CAG AAA      555
Ala Gly Pro Glu Gly Ser Thr Arg His Ala Ala Ser Lys Gln Lys
 150             155                 160

TAC CTG GAG AAT TAC CTC AAC CGT CTC TTG ACC ATG TCT TTC TAT      600
Tyr Leu Glu Asn Tyr Leu Asn Arg Leu Leu Thr Met Ser Phe Tyr
 165             170                 175

CGC AAC TAC CAT GCC ATG ACA GAG TTC CTG GAA GTC AGT CAG CTG      645
Arg Asn Tyr His Ala Met Thr Glu Phe Leu Glu Val Ser Gln Leu
 180             185                 190

TCC TTT ATC CCG GAA TTG GGC CGC AAA GGA CTG GAG GGG ATG ATC      690
Ser Phe Ile Pro Glu Leu Gly Arg Lys Gly Leu Glu Gly Met Ile
 195             200                 205

CGG AAG CGC TCA GGT GGC CAC CGT GTT TCT GGC CTC ACC TGC TGT      735
Arg Lys Arg Ser Gly Gly His Arg Val Ser Gly Leu Thr Cys Cys
 210             215                 220

GGC CGA GAC CAA GTT TGT TAT CGC TGG TCC AAG AGG TGG CTG GTG      780
Gly Arg Asp Gln Val Cys Tyr Arg Trp Ser Lys Arg Trp Leu Val
 225             230                 235

GTG AAG GAC TCC TTC CTG CTG TAC ATG TGC CTC GAG ACA GGT GCC      825
Val Lys Asp Ser Phe Leu Leu Tyr Met Cys Leu Glu Thr Gly Ala
 240             245                 250

ATC TCA TTT GTT CAG CTC TTT GAC CCT GGC TTT GAG GTG CAA GTG      870
Ile Ser Phe Val Gln Leu Phe Asp Pro Gly Phe Glu Val Gln Val
 255             260                 265

GGG AAA AGG AGC ACG GAG GCA CGG CAC GGC GTG CGG ATC GAT ACC      915
Gly Lys Arg Ser Thr Glu Ala Arg His Gly Val Arg Ile Asp Thr
```

```
                    270                           275                           280
TCC  CAC  AGG  TCC  TTG  ATT  CTC  AAG  TGC  AGC  AGC  TAC  CGG  CAG  GCA         960
Ser  His  Arg  Ser  Leu  Ile  Leu  Lys  Cys  Ser  Ser  Tyr  Arg  Gln  Ala
285                 290                           295

CGG  TGG  TGG  GCC  CAA  GAG  ATC  ACT  GAG  CTG  GCA  CAG  GGC  CCA  GGC        1005
Arg  Trp  Trp  Ala  Gln  Glu  Ile  Thr  Glu  Leu  Ala  Gln  Gly  Pro  Gly
300                 305                           310

AGA  GAC  TTC  CTA  CAG  CTG  CAC  CGG  CAT  GAC  AGC  TAC  GCC  CCA  CCC        1050
Arg  Asp  Phe  Leu  Gln  Leu  His  Arg  His  Asp  Ser  Tyr  Ala  Pro  Pro
315                 320                           325

CGG  CCT  GGG  ACC  TTG  GCC  CGG  TGG  TTT  GTG  AAT  GGG  GCA  GGT  TAC        1095
Arg  Pro  Gly  Thr  Leu  Ala  Arg  Trp  Phe  Val  Asn  Gly  Ala  Gly  Tyr
330                 335                           340

TTT  GCT  GCT  GTG  GCA  GAT  GCC  ATC  CTT  CGA  GCT  CAA  GAG  GAG  ATT        1140
Phe  Ala  Ala  Val  Ala  Asp  Ala  Ile  Leu  Arg  Ala  Gln  Glu  Glu  Ile
345                 350                           355

TTC  ATC  ACA  GAC  TGG  TGG  TTG  AGT  CCT  GAG  GTT  TAC  CTG  AAG  CGT        1185
Phe  Ile  Thr  Asp  Trp  Trp  Leu  Ser  Pro  Glu  Val  Tyr  Leu  Lys  Arg
360                 365                           370

CCG  GCC  CAT  TCA  GAT  GAC  TGG  AGA  CTG  GAC  ATT  ATG  CTC  AAG  AGG        1230
Pro  Ala  His  Ser  Asp  Asp  Trp  Arg  Leu  Asp  Ile  Met  Leu  Lys  Arg
375                 380                           385

AAG  GCG  GAG  GAG  GGT  GTC  CGT  GTG  TCT  ATT  CTG  CTG  TTT  AAA  GAA        1275
Lys  Ala  Glu  Glu  Gly  Val  Arg  Val  Ser  Ile  Leu  Leu  Phe  Lys  Glu
390                 395                           400

GTG  GAA  TTG  GCC  TTG  GGC  ATC  AAC  AGT  GGC  TAT  AGC  AAG  AAG  GCG        1320
Val  Glu  Leu  Ala  Leu  Gly  Ile  Asn  Ser  Gly  Tyr  Ser  Lys  Lys  Ala
405                 410                           415

CTG  ATG  CTG  CTG  CAC  CCC  AAC  ATA  AAG  GTG  ATG  CGT  CAC  CCA  GAC        1365
Leu  Met  Leu  Leu  His  Pro  Asn  Ile  Lys  Val  Met  Arg  His  Pro  Asp
420                 425                           430

CAA  GTG  ACG  TTG  TGG  GCC  CAT  CAT  GAG  AAG  CTC  CTG  GTG  GTG  GAC        1410
Gln  Val  Thr  Leu  Trp  Ala  His  His  Glu  Lys  Leu  Leu  Val  Val  Asp
435                 440                           445

CAA  GTG  GTA  GCA  TTC  CTG  GGG  GGA  CTG  GAC  CTT  GCC  TAT  GGC  CGC        1455
Gln  Val  Val  Ala  Phe  Leu  Gly  Gly  Leu  Asp  Leu  Ala  Tyr  Gly  Arg
450                 455                           460

TGG  GAT  GAC  CTG  CAC  TAC  CGA  CTG  ACT  GAC  CTT  GGA  GAC  TCC  TCT        1500
Trp  Asp  Asp  Leu  His  Tyr  Arg  Leu  Thr  Asp  Leu  Gly  Asp  Ser  Ser
465                 470                           475

GAA  TCA  GCT  GCC  TCC  CAG  CCT  CCC  ACC  CCG  CGC  CCA  GAC  TCA  CCA        1545
Glu  Ser  Ala  Ala  Ser  Gln  Pro  Pro  Thr  Pro  Arg  Pro  Asp  Ser  Pro
480                 485                           490

GCC  ACC  CCA  GAC  CTC  TCT  CAC  AAC  CAA  TTC  TTC  TGG  CTG  GGC  AAG        1590
Ala  Thr  Pro  Asp  Leu  Ser  His  Asn  Gln  Phe  Phe  Trp  Leu  Gly  Lys
495                 500                           505

GAC  TAC  AGC  AAT  CTT  ATC  ACC  AAT  GAC  TGG  GTG  CAG  CTG  GAC  CGG        1635
Asp  Tyr  Ser  Asn  Leu  Ile  Thr  Asn  Asp  Trp  Val  Gln  Leu  Asp  Arg
510                 515                           520

CCT  TTC  GAA  GAT  TTC  ATT  GAC  AGG  GAG  ACG  ACC  CCT  CGG  ATG  CCA        1680
Pro  Phe  Glu  Asp  Phe  Ile  Asp  Arg  Glu  Thr  Thr  Pro  Arg  Met  Pro
525                 530                           535

TGG  CGG  GAC  GTT  GGG  GTG  GTC  GTC  CAT  GGC  CTA  CCG  GCC  CGG  GAC        1725
Trp  Arg  Asp  Val  Gly  Val  Val  Val  His  Gly  Leu  Pro  Ala  Arg  Asp
540                 545                           550

CTT  GCC  CGG  CAC  TTC  ATC  CAG  CGC  TGG  AAC  TTC  ACC  AAG  ACC  ACC        1770
Leu  Ala  Arg  His  Phe  Ile  Gln  Arg  Trp  Asn  Phe  Thr  Lys  Thr  Thr
555                 560                           565

AAG  GCC  AAG  TAC  AAG  ACT  CCC  ACA  TAC  CCC  TAC  CTG  CTT  CCC  AAG        1815
Lys  Ala  Lys  Tyr  Lys  Thr  Pro  Thr  Tyr  Pro  Tyr  Leu  Leu  Pro  Lys
```

|     |     |     |     |     |     |     |     |     |     |     |     |     |     |     |      |
| --- | --- | --- | --- | --- | --- | --- | --- | --- | --- | --- | --- | --- | --- | --- | ---- |
| 570 |     |     |     |     |     | 575 |     |     |     |     | 580 |     |     |     |      |
| TCT | ACC | AGC | ACG | GCC | AAT | CAG | CTC | CCC | TTC | ACA | CTT | CCA | GGA | GGG | 1860 |
| Ser | Thr | Ser | Thr | Ala | Asn | Gln | Leu | Pro | Phe | Thr | Leu | Pro | Gly | Gly |      |
| 585 |     |     |     |     | 590 |     |     |     |     | 595 |     |     |     |     |      |
| CAG | TGC | ACC | ACC | GTA | CAG | GTC | TTG | CGA | TCA | GTG | GAC | CGC | TGG | TCA | 1905 |
| Gln | Cys | Thr | Thr | Val | Gln | Val | Leu | Arg | Ser | Val | Asp | Arg | Trp | Ser |      |
| 600 |     |     |     |     | 605 |     |     |     |     | 610 |     |     |     |     |      |
| GCA | GGG | ACT | CTG | GAG | AAC | TCC | ATC | CTC | AAT | GCC | TAC | CTG | CAC | ACC | 1950 |
| Ala | Gly | Thr | Leu | Glu | Asn | Ser | Ile | Leu | Asn | Ala | Tyr | Leu | His | Thr |      |
| 615 |     |     |     |     | 620 |     |     |     |     | 625 |     |     |     |     |      |
| ATC | AGG | GGG | AGC | CAG | CAC | TTC | CTC | TAC | ATT | GAG | AAT | CAG | TTC | TTC | 1995 |
| Ile | Arg | Gly | Ser | Gln | His | Phe | Leu | Tyr | Ile | Glu | Asn | Gln | Phe | Phe |      |
| 630 |     |     |     |     | 625 |     |     |     |     | 640 |     |     |     |     |      |
| ATT | AGC | TGC | TCA | GAT | GGG | CGG | ACG | GTT | CTG | AAC | AAG | GTG | GGC | GAT | 2040 |
| Ile | Ser | Cys | Ser | Asp | Gly | Arg | Thr | Val | Leu | Asn | Lys | Val | Gly | Asp |      |
| 645 |     |     |     |     | 650 |     |     |     |     | 655 |     |     |     |     |      |
| GAG | ATT | GTG | GAC | AGA | ATC | CTG | AAG | GCC | CAC | AAA | CAG | GGG | TGG | TGT | 2085 |
| Glu | Ile | Val | Asp | Arg | Ile | Leu | Lys | Ala | His | Lys | Gln | Gly | Trp | Cys |      |
| 660 |     |     |     |     | 665 |     |     |     |     | 670 |     |     |     |     |      |
| TAC | CGA | GTC | TAC | GTG | CTT | TTG | CCC | TTA | CTC | CCT | GGC | TTC | GAG | GGT | 2130 |
| Tyr | Arg | Val | Tyr | Val | Leu | Leu | Pro | Leu | Leu | Pro | Gly | Phe | Glu | Gly |      |
| 675 |     |     |     |     | 680 |     |     |     |     | 685 |     |     |     |     |      |
| GAC | ATC | TCC | ACG | GGC | GGT | GGC | AAG | TCC | ATC | CAG | GCC | ATT | CTG | CAC | 2175 |
| Asp | Ile | Ser | Thr | Gly | Gly | Gly | Lys | Ser | Ile | Gln | Ala | Ile | Leu | His |      |
| 690 |     |     |     |     | 695 |     |     |     |     | 700 |     |     |     |     |      |
| TTT | ACT | TAC | AGG | ACC | CTG | TGT | CGT | GGG | GAG | TAT | TCA | ATC | CTG | CAT | 2220 |
| Phe | Thr | Tyr | Arg | Thr | Leu | Cys | Arg | Gly | Glu | Tyr | Ser | Ile | Leu | His |      |
| 705 |     |     |     |     | 710 |     |     |     |     | 715 |     |     |     |     |      |
| CGC | CTT | AAA | GCA | GCC | ATG | GGG | ACA | GCA | TGG | CGG | GAC | TAT | ATT | TCC | 2265 |
| Arg | Leu | Lys | Ala | Ala | Met | Gly | Thr | Ala | Trp | Arg | Asp | Tyr | Ile | Ser |      |
| 720 |     |     |     |     | 725 |     |     |     |     | 730 |     |     |     |     |      |
| ATC | TGC | GGG | CTT | CGT | ACA | CAC | GGA | GAG | CTG | GGC | GGG | CAC | CCC | GTC | 2310 |
| Ile | Cys | Gly | Leu | Arg | Thr | His | Gly | Glu | Leu | Gly | Gly | His | Pro | Val |      |
| 735 |     |     |     |     | 740 |     |     |     |     | 745 |     |     |     |     |      |
| TCG | GAG | CTC | ATC | TAC | ATC | CAC | AGC | AAG | GTG | CTC | ATC | GCA | GAT | GAC | 2355 |
| Ser | Glu | Leu | Ile | Tyr | Ile | His | Ser | Lys | Val | Leu | Ile | Ala | Asp | Asp |      |
| 750 |     |     |     |     | 755 |     |     |     |     | 760 |     |     |     |     |      |
| CGG | ACA | GTC | ATC | ATT | GAT | TCT | GCA | AAC | ATC | AAT | GAC | CGG | AGC | TTG | 2400 |
| Arg | Thr | Val | Ile | Ile | Asp | Ser | Ala | Asn | Ile | Asn | Asp | Arg | Ser | Leu |      |
| 765 |     |     |     |     | 770 |     |     |     |     | 775 |     |     |     |     |      |
| CTG | GGG | AAG | CGG | GAC | AGT | GAG | CTG | GCC | GTG | CTA | ATC | GAG | GAC | ACA | 2445 |
| Leu | Gly | Lys | Arg | Asp | Ser | Glu | Leu | Ala | Val | Leu | Ile | Glu | Asp | Thr |      |
| 780 |     |     |     |     | 785 |     |     |     |     | 790 |     |     |     |     |      |
| GAG | ACG | GAA | CCA | TCC | CTC | ATG | AAT | GGG | GCA | GAG | TAT | CAG | GCG | GGC | 2490 |
| Glu | Thr | Glu | Pro | Ser | Leu | Met | Asn | Gly | Ala | Glu | Tyr | Gln | Ala | Gly |      |
| 795 |     |     |     |     | 800 |     |     |     |     | 805 |     |     |     |     |      |
| AGG | TTT | GCC | TTG | AGT | CTG | CGG | AAG | CAC | TGC | TTC | AGT | GTG | ATT | CTT | 2535 |
| Arg | Phe | Ala | Leu | Ser | Leu | Arg | Lys | His | Cys | Phe | Ser | Val | Ile | Leu |      |
| 810 |     |     |     |     | 815 |     |     |     |     | 820 |     |     |     |     |      |
| GGA | GCA | AAT | ACC | CGG | CCA | GAC | TTG | GAT | CTC | CGA | GAC | CCC | ATC | TGT | 2580 |
| Gly | Ala | Asn | Thr | Arg | Pro | Asp | Leu | Asp | Leu | Arg | Asp | Pro | Ile | Cys |      |
| 825 |     |     |     |     | 830 |     |     |     |     | 835 |     |     |     |     |      |
| GAT | GAC | TTC | TTC | CAG | TTG | TGG | CAA | GAC | ATG | GCT | GAG | AGC | AAC | GCC | 2625 |
| Asp | Asp | Phe | Phe | Gln | Leu | Trp | Gln | Asp | Met | Ala | Glu | Ser | Asn | Ala |      |
| 840 |     |     |     |     | 845 |     |     |     |     | 850 |     |     |     |     |      |
| AAT | ATC | TAT | GAG | CAG | ATC | TTC | CGC | TGC | CTG | CCA | TCC | AAT | GCC | ACG | 2670 |
| Asn | Ile | Tyr | Glu | Gln | Ile | Phe | Arg | Cys | Leu | Pro | Ser | Asn | Ala | Thr |      |
| 855 |     |     |     |     | 860 |     |     |     |     | 865 |     |     |     |     |      |
| CGT | TCC | CTG | CGG | ACT | CTC | CGG | GAG | TAC | GTG | GCC | GTG | GAG | CCC | TTG | 2715 |
| Arg | Ser | Leu | Arg | Thr | Leu | Arg | Glu | Tyr | Val | Ala | Val | Glu | Pro | Leu |      |

```
                    870                     875                     880

GCC  ACG  GTC  AGT  CCC  CCC  TTG  GCT  CGG  TCT  GAG  CTC  ACC  CAG  GTC      2760
       Ala  Thr  Val  Ser  Pro  Pro  Leu  Ala  Arg  Ser  Glu  Leu  Thr  Gln  Val
       885                      890                     895

CAG  GGC  CAC  CTG  GTC  CAC  TTC  CCC  CTC  AAG  TTC  CTA  GAG  GAT  GAG      2805
       Gln  Gly  His  Leu  Val  His  Phe  Pro  Leu  Lys  Phe  Leu  Glu  Asp  Glu
       900                      905                     910

TCT  TTG  CTG  CCC  CCG  CTG  GGT  AGC  AAG  GAG  GGC  AAG  ATC  CCC  CTA      2850
       Ser  Leu  Leu  Pro  Pro  Leu  Gly  Ser  Lys  Glu  Gly  Lys  Ile  Pro  Leu
       915                      920                     925

GAA  GTG  TGG  ACA  TAG                                                        2865
       Glu  Val  Trp  Thr
       930

TTGAGGCCCC   CGTCAGGGAG   AGGTCACCAG   CTGCTGTGCC   CCACCACGTC                  2915

TGGCTCCCTG   CCCCTTAACC   CCAAGGACTG   AGGGCAGTGC   CCTTTGAGAT                  2965

CTGGGGAGGC   AGGCATTCCT   GAAGGGAACT   AGAGGTGTTA   CAGAGGACCC                  3015

TTACGTGAGA   AATAGCTGAA   AAGGGCACTC   CCAACCCTGG   GCTGGGGAGG                  3065

AGGAGAGAGT   CCCAGAGCTC   ATCCCCCTG    CTGCCCAGTG   CAAACCACTT                  3115

CTCCATGCTG   CAAAGGAGAA   GCACAGCTCC   TGCCAGGGTG   AGCAGGGTCA                  3165

AGCCTCTTAT   TCCAGGAGAA   GGGGGCTCTG   CCCCAGGCCC   TACTACCCAT                  3215

TGTTCCCTTC   CTCTTCCTGC   CCTTGAACCC   CCTCCCTGTC   CAGGGCCCT                   3265

CCCAGCCCAT   TGCTGCCAAG   GTGGAGGGAA   GGATAAAGCC   ACTTCTGGCT                  3315

TCAGCCCCCA   CCAGGGGAAG   GAAGGAGGGC   ACATTAACTC   CCTCCACCAG                  3365

CCTGCTGACA   GACACTAACT   TTGTATCCGT   TCAATAAGCA   TTTCATAAAA                  3415

AAAAAAAAA                                                                       3425
```

( 2 ) INFORMATION FOR SEQ ID NO:2:

( i ) SEQUENCE CHARACTERISTICS:
        ( A ) LENGTH: 1074
        ( B ) TYPE: amino acid
        ( C ) STRANDEDNESS: single
        ( D ) TOPOLOGY: linear ( i i ) MOLECULE TYPE: polypeptide ( i i i ) HYPOTHETICAL: no ( i v ) ANTI-SENSE: no ( v ) FRAGMENT TYPE:

( v i ) ORIGINAL SOURCE:
        ( A ) ORGANISM: homo sapien
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: hPLD1

(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:2:

(xi) SEQUENCE DESCRIPTION:SEQ ID NO:2:

| Met | Ser | Leu | Lys | Asn | Glu | Pro | Arg | Val | Asn | Thr | Ser | Ala | Leu | Gln |
|---|---|---|---|---|---|---|---|---|---|---|---|---|---|---|
| 1 | | | | 5 | | | | | 10 | | | | | 15 |
| Lys | Ile | Ala | Ala | Asp | Met | Ser | Asn | Ile | Ile | Glu | Asn | Leu | Asp | Thr |
| | | | | 20 | | | | | 25 | | | | | 30 |
| Arg | Glu | Leu | His | Phe | Glu | Gly | Glu | Glu | Val | Asp | Tyr | Asp | Val | Ser |
| | | | | 35 | | | | | 40 | | | | | 45 |
| Pro | Ser | Asp | Pro | Lys | Ile | Gln | Glu | Val | Tyr | Ile | Pro | Phe | Ser | Ala |
| | | | | 50 | | | | | 55 | | | | | 60 |
| Ile | Tyr | Asn | Thr | Gln | Gly | Phe | Lys | Glu | Pro | Asn | Ile | Gln | Thr | Tyr |
| | | | | 65 | | | | | 70 | | | | | 75 |
| Leu | Ser | Gly | Cys | Pro | Ile | Lys | Ala | Gln | Val | Leu | Glu | Val | Glu | Arg |
| | | | | 80 | | | | | 85 | | | | | 90 |
| Phe | Thr | Ser | Thr | Thr | Arg | Val | Pro | Ser | Ile | Asn | Leu | Tyr | Thr | Ile |
| | | | | 95 | | | | | 100 | | | | | 105 |
| Glu | Leu | Thr | His | Gly | Glu | Phe | Lys | Trp | Gln | Val | Lys | Arg | Lys | Phe |
| | | | | 110 | | | | | 115 | | | | | 120 |
| Lys | His | Phe | Gln | Glu | Phe | His | Arg | Glu | Leu | Leu | Lys | Tyr | Lys | Ala |
| | | | | 125 | | | | | 130 | | | | | 135 |
| Phe | Ile | Arg | Ile | Pro | Ile | Pro | Thr | Arg | Arg | His | Thr | Phe | Arg | Arg |
| | | | | 140 | | | | | 145 | | | | | 150 |
| Gln | Asn | Val | Arg | Glu | Glu | Pro | Arg | Glu | Met | Pro | Ser | Leu | Pro | Arg |
| | | | | 155 | | | | | 160 | | | | | 165 |
| Ser | Ser | Glu | Asn | Met | Ile | Arg | Glu | Glu | Gln | Phe | Leu | Gly | Arg | Arg |
| | | | | 170 | | | | | 175 | | | | | 180 |
| Lys | Gln | Leu | Glu | Asp | Tyr | Leu | Thr | Lys | Ile | Leu | Lys | Met | Pro | Met |
| | | | | 185 | | | | | 190 | | | | | 195 |
| Tyr | Arg | Asn | Tyr | His | Ala | Thr | Thr | Glu | Phe | Leu | Asp | Ile | Ser | Gln |
| | | | | 200 | | | | | 205 | | | | | 210 |
| Leu | Ser | Phe | Ile | His | Asp | Leu | Gly | Pro | Lys | Gly | Ile | Glu | Gly | Met |
| | | | | 215 | | | | | 220 | | | | | 225 |
| Ile | Met | Lys | Arg | Ser | Gly | Gly | His | Arg | Ile | Pro | Gly | Leu | Asn | Cys |
| | | | | 230 | | | | | 235 | | | | | 240 |
| Cys | Gly | Gln | Gly | Arg | Ala | Cys | Tyr | Arg | Trp | Ser | Lys | Arg | Trp | Leu |
| | | | | 245 | | | | | 250 | | | | | 255 |
| Ile | Val | Lys | Asp | Ser | Phe | Leu | Leu | Tyr | Met | Lys | Pro | Asp | Ser | Gly |
| | | | | 260 | | | | | 265 | | | | | 270 |
| Ala | Ile | Ala | Phe | Val | Leu | Leu | Val | Asp | Lys | Glu | Phe | Lys | Ile | Lys |
| | | | | 275 | | | | | 280 | | | | | 285 |
| Val | Gly | Lys | Lys | Glu | Thr | Glu | Thr | Lys | Tyr | Gly | Ile | Arg | Ile | Asp |
| | | | | 290 | | | | | 295 | | | | | 300 |
| Asn | Leu | Ser | Arg | Thr | Leu | Ile | Leu | Lys | Cys | Asn | Ser | Tyr | Arg | His |

```
                                    305                         310                         315
Ala  Arg  Trp  Trp  Gly  Ala  Ile  Glu  Glu  Phe  Ile  Gln  Lys  His
                    320                         325                         330

Gly  Thr  Asn  Phe  Leu  Lys  Asp  His  Arg  Phe  Gly  Ser  Tyr  Ala  Ala
                    335                         340                         345

Ile  Gln  Glu  Asn  Ala  Leu  Ala  Lys  Trp  Tyr  Val  Asn  Ala  Lys  Gly
                    350                         355                         360

Tyr  Phe  Glu  Asp  Val  Ala  Asn  Ala  Met  Glu  Glu  Ala  Asn  Glu  Glu
                    365                         370                         375

Ile  Phe  Ile  Thr  Asp  Trp  Trp  Leu  Ser  Pro  Glu  Ile  Phe  Leu  Lys
                    380                         385                         390

Arg  Pro  Val  Val  Glu  Gly  Asn  Arg  Trp  Arg  Leu  Asp  Cys  Ile  Leu
                    395                         400                         405

Lys  Arg  Lys  Ala  Gln  Gln  Gly  Val  Arg  Ile  Phe  Ile  Met  Leu  Tyr
                    410                         415                         420

Lys  Glu  Val  Glu  Leu  Ala  Leu  Gly  Ile  Asn  Ser  Glu  Tyr  Thr  Lys
                    425                         430                         435

Arg  Thr  Leu  Met  Arg  Leu  His  Pro  Asn  Ile  Lys  Val  Met  Arg  His
                    440                         445                         450

Pro  Asp  His  Val  Ser  Ser  Thr  Val  Tyr  Leu  Trp  Ala  His  His  Glu
                    455                         460                         465

Lys  Leu  Val  Ile  Ile  Asp  Gln  Ser  Val  Ala  Phe  Val  Gly  Gly  Ile
                    470                         475                         480

Asp  Leu  Ala  Tyr  Gly  Arg  Trp  Asp  Asp  Asn  Glu  His  Arg  Leu  Thr
                    485                         490                         495

Asp  Val  Gly  Ser  Val  Lys  Arg  Val  Thr  Ser  Gly  Pro  Ser  Leu  Gly
                    500                         505                         510

Ser  Leu  Pro  Pro  Ala  Ala  Met  Glu  Ser  Met  Glu  Ser  Leu  Arg  Leu
                    515                         520                         525

Lys  Asp  Lys  Asn  Glu  Pro  Val  Gln  Asn  Leu  Pro  Ile  Gln  Lys  Ser
                    530                         535                         540

Ile  Asp  Asp  Val  Asp  Ser  Lys  Leu  Lys  Gly  Ile  Gly  Lys  Pro  Arg
                    545                         550                         555

Lys  Phe  Ser  Lys  Phe  Ser  Leu  Tyr  Lys  Gln  Leu  His  Arg  His  His
                    560                         565                         570

Leu  His  Asp  Ala  Asp  Ser  Ile  Ser  Ser  Ile  Asp  Ser  Thr  Ser  Ser
                    575                         580                         585

Tyr  Phe  Asn  His  Tyr  Arg  Ser  His  His  Asn  Leu  Ile  His  Gly  Leu
                    590                         595                         600

Lys  Pro  His  Phe  Lys  Leu  Phe  His  Pro  Ser  Ser  Glu  Ser  Glu  Gln
                    605                         610                         615

Gly  Leu  Thr  Arg  Pro  His  Ala  Asp  Thr  Gly  Ser  Ile  Arg  Ser  Leu
                    620                         625                         630

Gln  Thr  Gly  Val  Gly  Glu  Leu  His  Gly  Glu  Thr  Arg  Phe  Trp  His
                    635                         640                         645

Gly  Lys  Asp  Tyr  Cys  Asn  Phe  Val  Phe  Lys  Asp  Trp  Val  Gln  Leu
                    650                         655                         660

Asp  Lys  Pro  Phe  Ala  Asp  Phe  Ile  Asp  Arg  Tyr  Ser  Thr  Pro  Arg
                    665                         670                         675

Met  Pro  Trp  His  Asp  Ile  Ala  Ser  Ala  Val  His  Gly  Lys  Ala  Ala
                    680                         685                         690

Arg  Asp  Val  Ala  Arg  His  Phe  Ile  Gln  Arg  Trp  Asn  Phe  Thr  Lys
                    695                         700                         705
```

```
Ile  Met  Lys  Ser  Lys  Tyr  Arg  Ser  Leu  Ser  Tyr  Pro  Phe  Leu  Leu
               710                 715                      720

Pro  Lys  Ser  Gln  Thr  Thr  Ala  His  Glu  Leu  Arg  Tyr  Gln  Val  Pro
               725                 730                      735

Gly  Ser  Val  His  Ala  Asn  Val  Gln  Leu  Leu  Arg  Ser  Ala  Ala  Asp
               740                 745                      750

Trp  Ser  Ala  Gly  Ile  Lys  Tyr  His  Glu  Ser  Ile  His  Ala  Ala
               755                 760                      765

Tyr  Val  His  Val  Ile  Glu  Asn  Ser  Arg  His  Tyr  Ile  Tyr  Ile  Glu
               770                 775                      780

Asn  Gln  Phe  Phe  Ile  Ser  Cys  Ala  Asp  Asp  Lys  Val  Val  Phe  Asn
               785                 790                      795

Lys  Ile  Gly  Asp  Ala  Ile  Ala  Gln  Arg  Ile  Leu  Lys  Ala  His  Arg
               800                 805                      810

Glu  Asn  Gln  Lys  Tyr  Arg  Val  Tyr  Val  Val  Ile  Pro  Leu  Leu  Pro
               815                 820                      825

Gly  Phe  Glu  Gly  Asp  Ile  Ser  Thr  Gly  Gly  Asn  Ala  Leu  Gln
               830                 835                      840

Ala  Ile  Met  His  Phe  Asn  Tyr  Arg  Thr  Met  Cys  Arg  Gly  Glu  Asn
               845                 850                      855

Ser  Ile  Leu  Gly  Gln  Leu  Lys  Ala  Glu  Leu  Gly  Asn  Gln  Trp  Ile
               860                 865                      870

Asn  Tyr  Ile  Ser  Phe  Cys  Gly  Leu  Arg  Thr  His  Ala  Glu  Leu  Glu
               875                 880                      885

Gly  Asn  Leu  Val  Thr  Glu  Leu  Ile  Tyr  Val  His  Ser  Lys  Leu  Leu
               890                 895                      900

Ile  Ala  Asp  Asp  Asn  Thr  Val  Ile  Ile  Gly  Ser  Ala  Asn  Ile  Asn
               905                 910                      915

Asp  Arg  Ser  Met  Leu  Gly  Lys  Arg  Asp  Ser  Glu  Met  Ala  Val  Ile
               920                 925                      930

Val  Gln  Asp  Thr  Glu  Thr  Val  Pro  Ser  Val  Met  Asp  Gly  Lys  Glu
               935                 940                      945

Tyr  Gln  Ala  Gly  Arg  Phe  Ala  Arg  Gly  Leu  Arg  Leu  Gln  Cys  Phe
               950                 955                      960

Arg  Val  Val  Leu  Gly  Tyr  Leu  Asp  Asp  Pro  Ser  Glu  Asp  Ile  Gln
               965                 970                      975

Asp  Pro  Val  Ser  Asp  Lys  Phe  Phe  Lys  Glu  Val  Trp  Val  Ser  Thr
               980                 985                      990

Ala  Ala  Arg  Asn  Ala  Thr  Ile  Tyr  Asp  Lys  Val  Phe  Arg  Cys  Leu
               995                 1000                     1005

Pro  Asn  Asp  Glu  Val  His  Asn  Leu  Ile  Gln  Leu  Arg  Asp  Phe  Ile
               1010                1015                     1020

Asn  Lys  Pro  Val  Leu  Ala  Lys  Glu  Asp  Pro  Ile  Arg  Ala  Glu  Glu
               1025                1030                     1035

Glu  Leu  Lys  Lys  Ile  Arg  Gly  Phe  Leu  Val  Gln  Phe  Pro  Phe  Tyr
               1040                1045                     1050

Phe  Leu  Ser  Glu  Glu  Ser  Leu  Leu  Pro  Ser  Val  Gly  Thr  Lys  Glu
               1055                1060                     1065

Ala  Ile  Val  Pro  Met  Glu  Val  Trp  Thr
               1070
```

( 2 ) INFORMATION FOR SEQ ID NO:3:

( i ) SEQUENCE CHARACTERISTICS:
        ( A ) LENGTH: 19

( B ) TYPE: amino acid
            ( C ) STRANDEDNESS: single
            ( D ) TOPOLOGY: linear ( i i ) MOLECULE TYPE: polypeptide ( i i i ) HYPOTHETICAL: no ( i v ) ANTI-SENSE: no ( v ) FRAGMENT TYPE:

( v i ) ORIGINAL SOURCE:
            ( A ) ORGANISM: castor bean
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( v i i ) IMMEDIATE SOURCE:
            ( A ) LIBRARY:
            ( B ) CLONE:

( v i i i ) POSITION IN GENOME:
            ( A ) CHROMOSOME/SEGMENT:
            ( B ) MAP POSITION:
            ( C ) UNITS:

( i x ) FEATURE:
            ( A ) NAME/KEY: PCPLD fragment
            ( B ) LOCATION:
            ( C ) IDENTIFICATION METHOD:
            ( D ) OTHER INFORMATION:

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:3:

( x i ) SEQUENCE DESCRIPTION:SEQ ID NO:3:

Gln Arg Ser Met Asp Gly Ala Arg Asp Ser Glu Ile Ala Met Gly
                  5                   1 0                 1 5
Ala Tyr Gln Pro ( 2 ) INFORMATION FOR SEQ ID NO:4:

( i ) SEQUENCE CHARACTERISTICS:
            ( A ) LENGTH: 19
            ( B ) TYPE: amino acid
            ( C ) STRANDEDNESS: single
            ( D ) TOPOLOGY: linear ( i i ) MOLECULE TYPE: polypeptide ( i i i ) HYPOTHETICAL: no ( i v ) ANTI-SENSE: no ( v ) FRAGMENT TYPE:

( v i ) ORIGINAL SOURCE:
            ( A ) ORGANISM: yeast
            ( B ) STRAIN:
            ( C ) INDIVIDUAL ISOLATE:
            ( D ) DEVELOPMENTAL STAGE:

(E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY: PCPLD fragment
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:4:

(xi) SEQUENCE DESCRIPTION:SEQ ID NO:4:

Glu Arg Ser Gln Leu Gly Asn Arg Asp Ser Glu Val Ala Ile Leu
                 5                   10                  15

Ile Arg Asp Thr (2) INFORMATION FOR SEQ ID NO:5:

(i) SEQUENCE CHARACTERISTICS:
                (A) LENGTH: 19
                (B) TYPE: amino acid
                (C) STRANDEDNESS: single
                (D) TOPOLOGY: linear (ii) MOLECULE TYPE: polypeptide (iii) HYPOTHETICAL: no (iv) ANTI-SENSE: no (v) FRAGMENT TYPE:

(vi) ORIGINAL SOURCE:
                (A) ORGANISM: yeast
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY: polypeptide fragment ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:5:

( x i ) SEQUENCE DESCRIPTION:SEQ ID NO:5:

```
Asp Arg Ser Leu Leu Gly Lys Arg Asp Ser Glu Leu Ala Val Leu
                  5                  10                  15
Ile Glu Asp Thr
```

( 2 ) INFORMATION FOR SEQ ID NO:6:

( i ) SEQUENCE CHARACTERISTICS:
        ( A ) LENGTH:24
        ( B ) TYPE:NUCLEIC ACID
        ( C ) STRANDEDNESS:single
        ( D ) TOPOLOGY:linear ( i i ) MOLECULE TYPE: oligonucleotide fragment ( i i i ) HYPOTHETICAL:no ( i v ) ANTI-SENSE:no ( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( i x ) FEATURE:
        ( A ) NAME/KEY: o.r83570.1
        ( B ) LOCATION:
        ( C ) IDENTIFICATION METHOD:
        ( D ) OTHER INFORMATION:

( x i ) SEQUENCE DESCRIPTION:SEQ ID NO:6:

GTATTCAATC CTGCATCGCC TTAA                                      24

( 2 ) INFORMATION FOR SEQ ID NO:7:

( i ) SEQUENCE CHARACTERISTICS:
        ( A ) LENGTH:27
        ( B ) TYPE:NUCLEIC ACID
        ( C ) STRANDEDNESS:single
        ( D ) TOPOLOGY:linear ( i i ) MOLECULE TYPE: oligonucleotide fragment ( i i i ) HYPOTHETICAL:no ( i v ) ANTI-SENSE:no ( v ) FRAGMENT TYPE:

( v i ) ORIGINAL SOURCE:

(A) ORGANISM:
                    (B) STRAIN:
                    (C) INDIVIDUAL ISOLATE:
                    (D) DEVELOPMENTAL STAGE:
                    (E) HAPLOTYPE:
                    (F) TISSUE TYPE:
                    (G) CELL TYPE:
                    (H) CELL LINE:
                    (I) ORGANELLE:

(ix) FEATURE:
                    (A) NAME/KEY: o.R83570.1R
                    (B) LOCATION:
                    (C) IDENTIFICATION METHOD:
                    (D) OTHER INFORMATION:

(xi) SEQUENCE DESCRIPTION:SEQ ID NO:7:

GTCATCTGCG ATGAGCACCT TGCTGTG                                                                        2 7

(2) INFORMATION FOR SEQ ID NO:8:

(i) SEQUENCE CHARACTERISTICS:
                    (A) LENGTH:21
                    (B) TYPE:NUCLEIC ACID
                    (C) STRANDEDNESS:single
                    (D) TOPOLOGY:linear (ii) MOLECULE TYPE: oligonucleotide fragment (iii) HYPOTHETICAL:no (iv) ANTI-SENSE:no (v) FRAGMENT TYPE:

(vi) ORIGINAL SOURCE:
                    (A) ORGANISM:
                    (B) STRAIN:
                    (C) INDIVIDUAL ISOLATE:
                    (D) DEVELOPMENTAL STAGE:
                    (E) HAPLOTYPE:
                    (F) TISSUE TYPE:
                    (G) CELL TYPE:
                    (H) CELL LINE:
                    (I) ORGANELLE:

(ix) FEATURE:
                    (A) NAME/KEY: o.sport.1R
                    (B) LOCATION:
                    (C) IDENTIFICATION METHOD:
                    (D) OTHER INFORMATION:

(xi) SEQUENCE DESCRIPTION:SEQ ID NO:8:

CTAGCTTATA ATACGACTCA C                                                                              2 1

(2) INFORMATION FOR SEQ ID NO:9:

(i) SEQUENCE CHARACTERISTICS:
                    (A) LENGTH:21
                    (B) TYPE:NUCLEIC ACID
                    (C) STRANDEDNESS:single
                    (D) TOPOLOGY:linear (ii) MOLECULE TYPE: oligonucleotide fragment (iii) HYPOTHETICAL:no (iv) ANTI-SENSE:no (v) FRAGMENT TYPE:

(vi) ORIGINAL SOURCE:
                    (A) ORGANISM:
                    (B) STRAIN:
                    (C) INDIVIDUAL ISOLATE:
                    (D) DEVELOPMENTAL STAGE:

( E ) HAPLOTYPE:
                    ( F ) TISSUE TYPE:
                    ( G ) CELL TYPE:
                    ( H ) CELL LINE:
                    ( I ) ORGANELLE:

( i x ) FEATURE:
                    ( A ) NAME/KEY: o.sport.1R
                    ( B ) LOCATION:
                    ( C ) IDENTIFICATION METHOD:
                    ( D ) OTHER INFORMATION:

( x i ) SEQUENCE DESCRIPTION:SEQ ID NO:9:

GACTCTAGCC TAGGCTTTTG C                                                         21

( 2 ) INFORMATION FOR SEQ ID NO:10:

( i ) SEQUENCE CHARACTERISTICS:
                    ( A ) LENGTH:21
                    ( B ) TYPE:NUCLEIC ACID
                    ( C ) STRANDEDNESS:single
                    ( D ) TOPOLOGY:linear ( i i ) MOLECULE TYPE: oligonucleotide fragment ( i i i ) HYPOTHETICAL:no ( i v ) ANTI-SENSE:no ( v ) FRAGMENT TYPE:

( v i ) ORIGINAL SOURCE:
                    ( A ) ORGANISM:
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( i x ) FEATURE:
                    ( A ) NAME/KEY: o.pld3.2R
                    ( B ) LOCATION:
                    ( C ) IDENTIFICATION METHOD:
                    ( D ) OTHER INFORMATION:

( x i ) SEQUENCE DESCRIPTION:SEQ ID NO:10:

CTCAGGACTC AACCACCAGT C                                                         21

( 2 ) INFORMATION FOR SEQ ID NO:11:

( i ) SEQUENCE CHARACTERISTICS:
                    ( A ) LENGTH:29
                    ( B ) TYPE:NUCLEIC ACID
                    ( C ) STRANDEDNESS:single
                    ( D ) TOPOLOGY:linear ( i i ) MOLECULE TYPE: oligonucleotide fragment ( i i i ) HYPOTHETICAL:no ( i v ) ANTI-SENSE:no ( v ) FRAGMENT TYPE:

( v i ) ORIGINAL SOURCE:
                    ( A ) ORGANISM:
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:

( I ) ORGANELLE:

( i x ) FEATURE:
            ( A ) NAME/KEY: PCR PRIMER
            ( B ) LOCATION:
            ( C ) IDENTIFICATION METHOD:
            ( D ) OTHER INFORMATION:

( x i ) SEQUENCE DESCRIPTION:SEQ ID NO:11:

GGCTCTAGAT ATTAATAGTA ATCAATTAC                                                  29

( 2 ) INFORMATION FOR SEQ ID NO:12:

( i ) SEQUENCE CHARACTERISTICS:
            ( A ) LENGTH:26
            ( B ) TYPE:NUCLEIC ACID
            ( C ) STRANDEDNESS:single
            ( D ) TOPOLOGY:linear ( i i ) MOLECULE TYPE: oligonucleotide fragment ( i i i ) HYPOTHETICAL:no ( i v ) ANTI-SENSE:no ( v ) FRAGMENT TYPE:

( v i ) ORIGINAL SOURCE:
            ( A ) ORGANISM:
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( i x ) FEATURE:
            ( A ) NAME/KEY: PCR PRIMER
            ( B ) LOCATION:
            ( C ) IDENTIFICATION METHOD:
            ( D ) OTHER INFORMATION:

( x i ) SEQUENCE DESCRIPTION:SEQ ID NO:12:

CCTCACGCAT GCACCATGGT AATAGC                                                     26

( 2 ) INFORMATION FOR SEQ ID NO:13:

( i ) SEQUENCE CHARACTERISTICS:
            ( A ) LENGTH:24
            ( B ) TYPE:NUCLEIC ACID
            ( C ) STRANDEDNESS:single
            ( D ) TOPOLOGY:linear ( i i ) MOLECULE TYPE: oligonucleotide fragment ( i i i ) HYPOTHETICAL:no ( i v ) ANTI-SENSE:no ( v ) FRAGMENT TYPE:

( v i ) ORIGINAL SOURCE:
            ( A ) ORGANISM:
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( i x ) FEATURE:
            ( A ) NAME/KEY: PCR PRIMER (B) LOCATION:
      (C) IDENTIFICATION METHOD:
      (D) OTHER INFORMATION:

(xi) SEQUENCE DESCRIPTION:SEQ ID NO:13:

GGTGCATGCG TGAGGCTCCG GTGC                                                              24

(2) INFORMATION FOR SEQ ID NO:14:

(i) SEQUENCE CHARACTERISTICS:
      (A) LENGTH:28
      (B) TYPE:NUCLEIC ACID
      (C) STRANDEDNESS:single
      (D) TOPOLOGY:linear (ii) MOLECULE TYPE: oligonucleotide fragment (iii) HYPOTHETICAL:no (iv) ANTI-SENSE:no (v) FRAGMENT TYPE:

(vi) ORIGINAL SOURCE:
      (A) ORGANISM:
      (B) STRAIN:
      (C) INDIVIDUAL ISOLATE:
      (D) DEVELOPMENTAL STAGE:
      (E) HAPLOTYPE:
      (F) TISSUE TYPE:
      (G) CELL TYPE:
      (H) CELL LINE:
      (I) ORGANELLE:

(ix) FEATURE:
      (A) NAME/KEY: PCR PRIMER
      (B) LOCATION:
      (C) IDENTIFICATION METHOD:
      (D) OTHER INFORMATION:

(xi) SEQUENCE DESCRIPTION:SEQ ID NO:14:

GTAGTTTTCA CGGTACCTGA AATGGAAG                                                          28

HUMAN PHOSPHATIDYLCHOLINE PHOSPHOLIPASE D

CROSS REFERENCE TO RELATED APPLICATIONS

This is a Continuation-in-Part Application of U.S. Provisional Application No. 60/008,768 filed Dec. 15, 1995.

TECHNICAL FIELD OF THE INVENTION

In general, the invention pertains to human polynucleotide sequences encoding for polypeptides having enzymatic activity relevant in cell signaling. The present application pertains in particular to mammalian phosphatidylcholine phospholipase D (PCPLD), specifically, human PCPLD (hPCPLD), to fragments and polypeptide analogs thereof and to polynucleotides encoding the same.

BACKGROUND OF THE INVENTION

Cell activation is associated with rapid upregulation of synthesis of phospholipids (PL) that includes phosphatidic acid (PA), diacylglycerol (DAG) and phosphatidylinositol (PI). PA's are a molecularly diverse group of phospholipid second messengers coupled to cellular activation and mitogenesis (Singer et al., *Exp. Opin. Invest. Drugs* 3:631–643, 1994. Compounds capable of modulating PA generation and hence altering a signal involved in cell activation may therefore be of therapeutic interest in the area of inflammation and oncology.

Lysophosphatidic acid acyltransferase (LPAAT) is an important enzyme in the synthesis of a specific species of PA in activated monocytic cells. (Rice et al., *Proc. Natl. Acad. Sci. USA* 91:3857–3861, 1994). PCPLD is another major enzyme class involved in the generation of PA through hydrolysis of phosphatidyl choline (PC) into PA and choline (Exton, *Biochim Biophys Acta* 1212:26–42, 1994). Okamura et al. report PCPLD protein purification from pig lung (Okamura et al., *J. Biol. Chem.* 269:31207–31213, 1994). Brown et al. report PCPLD protein purification from porcine brain (Brown et al., *J. Biol. Chem.* 270:14935–14943, 1995), and Vinggaard et al. discuss PCPLD isolation from human placenta (Vinggaard et al., *Biochim Biophys Acta* 1258:169–176, 1995).

In plant species, Wang et al. published results of cloning efforts with castor bean PCPLDs (Wang et al., *J. Biol Chem.* 269:20312–20317, 1994). Ueki et al. disclose PCPLD purified from rice and maize (Ueki et al., *Plant Cell Physiol.* 36:903–914, 1995); and Ella et al. and Rose et al. discuss PCPLD isolated and purified from yeast (Ella et al., *Biochem. J.* 314, 15–19, 1996; and Rose et al., *Proc. Natl. Acad. Sci.* 92: 12151–12155, 1995).

Most recently, Hammond et al. report cloning of a human isoform of PCPLD (hPLD1) (Hammond et al., *J Biol. Chem.* 270: 29640–29643, 1995). SEQ ID NO. 3 is a sequence listing of the amino acids of hPLD1. Based on a variety of biochemical studies including differential subcellular fractionation, distinct mechanism of activation, substrate specificity and different chromatographic properties, evidence for the existence of multiple phospholipase D (PLD) isoforms in mammalian cells is growing rapidly (Liscovitch, et al., *Chem. Phys. Lipids* 80: 37–44, 1996; Kiss, *Chem. Phys. Lipids* 80: 81–102). hPLD1 has approximately a 40% sequence homology with hPCPLD.

Although other mammalian PLD sequences have been cloned, heretofore the sequence of the disclosed PCPLD has not been obtained. Therefore, cloning cDNA isoforms of PLD that are closely related to other mammalian and plant isoforms of PLD would be useful in conducting discovery research to identify specific agents capable of modulating this enzyme. This invention provides one such unknown isoform, hPPCPLD.

SUMMARY OF THE INVENTION

The invention provides a cDNA sequence, polypeptide sequence, and transformed cells for producing isolated recombinant mammalian PCPLD. Such sequences may include: the incorporation of codons "preferred" for expression by selected nonmammalian hosts; the provision of sites for cleavage by restriction endonuclease enzymes; and the provision of additional initial, terminal or intermediate DNA sequences which facilitate construction of readily expressed vectors. The polypeptides of the invention have PCPLD activity and are known as hPCPLD. The invention also provides DNA sequences coding for microbial expression of polypeptide analogs or derivatives of PCFLD which differ from naturally-occurring forms in terms of the identity or location of one or more amino acid residues (i.e., deletion analogs containing less than all of the residues specified for PCPLD; substitution analogs such as [$Ser^{17}$]PCPLD, wherein one or more amino acid residues is added to a terminal or medial portion of the polypeptide) and which share some or all properties of naturally-occurring forms.

Novel DNA sequences of the invention include sequences useful for expression in procaryotic or eucaryotic host cells of polypeptides products, having at least a primary structural conformation and one or more of the biological properties of naturally-occurring PCPLD. The inventive DNA sequences specifically comprise, without limitation: a) the DNA sequence set forth in this specification or its complimentary strand; b) a DNA sequence which hybridizes (under hybridization conditions such as illustrated herein or more stringent conditions) to the DNA sequence set forth in this specification or to fragments thereof; and c) DNA sequences which, but for the degeneracy of the genetic code, would hybridize to the DNA sequences disclosed herein; and d) purified hPCPLD and antisense oligonucleotides for modulation of expression of the genetic code for hPCPLD polypeptide. Part (b) specifically includes, without limitation, genomic DNA sequences encoding allelic variant forms of hPCPLD, and part (c) includes, without limitation, manufactured DNA sequences encoding hPCPLD, fragments of hPCPLD and analogs of hPCPLD, said DNA sequences optionally incorporating codons facilitating translation messenger RNA in microbial hosts. In addition, the invention includes assays for screening test compounds for their ability to inhibit hPCPLD.

BRIEF DESCRIPTION OF THE DRAWINGS

As shown in FIG. 2, increasing concentrations of CT-2584 correspond to an increase in fluorescent intensity of the products corresponding to NBD-Pa-Bt, NBD-LPA-Bt, and NBD-PA bands on the TLC plate.

DETAILED DESCRIPTION OF PREFERRED EMBODIMENTS

Figure 1:
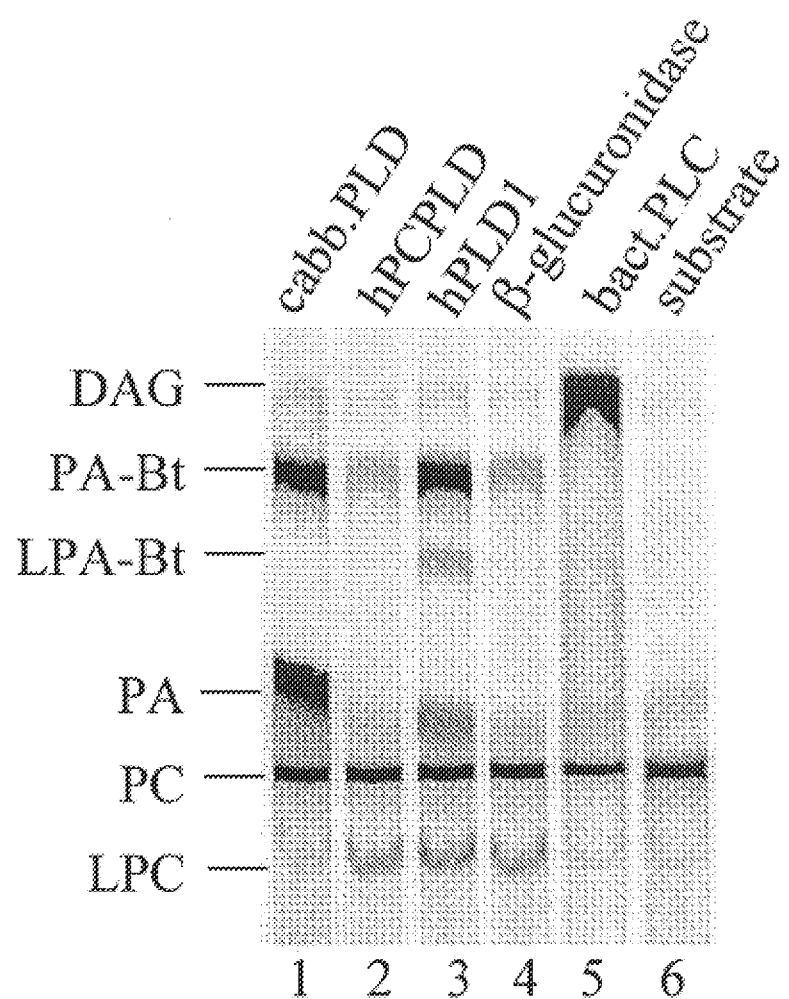
FIG. 1 shows TLC analysis of PCPLD activity in Sf9 cell extracts transfected with various Baculoviral constructs expressing hPCPLD and hPLD1 using a fluorescent-labeled PC substrate.

In the description that follows, a number of terms are utilized extensively. Definitions are provided to facilitate understanding of the invention.

Definitions

The term "isolated" applied throughout the specification to polypeptides refers to that level of purity in which the polypeptide is sufficiently free of other materials endogenous to the host from which the polypeptide is isolated such that any remaining materials do not materially affect the biological properties of the polypeptide.

The term "derived" as used throughout the specification in relation to the polypeptides of the invention, encompasses polypeptides obtained by isolation and purification from host cells, as well as polypeptides obtained by manipulation and expression of nucleotide sequences prepared from host cells. It also encompasses nucleotide sequences including genomic DNA, mRNA, cDNA synthesized from mRNA, and synthetic oligonucleotides having sequences corresponding to the inventive nucleotide sequences. It further encompasses synthetic polypeptide antigens prepared on the basis of the known amino acid sequences of the proteins of the invention.

The term "expression product" as used throughout the specification refers to materials produced by recombinant DNA techniques.

PCPLD catalyzes the hydrolysis of phospholipids to PA. The preferred substrate for this reaction is PC, a major mammalian cell-membrane constituent. Recombinant hPCPLD is useful in screening candidate drug compounds which inhibit or activate hPCPLD activity. The invention provides a cDNA sequence encoding a polypeptide having PCPLD enzymatic activity and comprising the DNA sequence set forth in SEQ ID NO. 1, shortened fragments thereof, or additional cDNA sequences, which due to the degeneracy of the genetic code encode a polypeptide of SEQ ID NO. 1 or biologically active fragments thereof or a sequence capable of hybridizing thereto under high stringency conditions. The invention further provides a polypeptide having PCPLD activity and comprising the amino acid sequence of SEQ ID NO. 1 or biologically active fragments thereof.

Also provided by the invention are vectors containing a DNA sequence encoding a mammalian PCPLD enzyme in operative association with an expression control sequence, and host cells, transformed with such vectors for use in producing recombinant PCPLD. The inventive vectors and transformed cells are employed in a process for producing recombinant mammalian PCPLD. In this process, a cell line transformed with a DNA sequence encoding an expression for a PCPLD enzyme in operative association with an expression control sequence, is cultured. The process may employ a number of known cells as host cells for expression of the PCPLD polypeptide, including, for example, mammalian cells, yeast cells, insect cells and bacterial cells.

Another aspect of this invention includes a method for identifying a pharmaceuticallyactive compound by determining if a selected compound is capable of inhibiting the activity of PCPLD for hydrolyzing PC to PA. A compound capable of such activity is capable of being a pharmaceutical compound useful for inhibiting a signal cascade in an inflammatory response.

The invention further provides a transformed cell that expresses active mammalian PCPLD and further comprises a means for determining if a drug candidate compound is therapeutically active by inhibiting or activating recombinant PCPLD activity.

Accordingly, hPCPLD is characterized by the 933 amino acids of SEQ ID NO. 1. The invention includes allelic variations (naturally-occurring base changes in the species population which may or may not result in an amino acid change) of the DNA sequences herein encoding active PCPLD polypeptides and active fragments thereof. The inventive DNA sequences further comprise those sequences which hybridize under stringent conditions (see, for example, Maniatis et al, *Molecular Cloning (A Laboratory Manual)*, Cold Spring Harbor Laboratory, pages 387–389, 1982) to the coding region (e.g., nucleotide #66 to nucleotide #2864). For example, one such high stringency hybridization condition is, for example, 4× SSC at 65° C., followed by washing in 0.1× SSC at 65° C. for thirty minutes. Alternatively, another high stringency hybridization condition is in 50% formamide, 4× SSC at 42° C. The present invention further includes DNA sequences which code for PCPLD polypeptides having PCPLD activity but differ in codon sequence due to degeneracies of the genetic code. Variations in the DNA sequences which are caused by point mutations or by induced modifications of the sequence of SEQ ID NO. 1, which enhance the activity of the encoded polypeptide or production of the encoded PCPLD polypeptide are also encompassed by the present invention.

Identification of Coding Sequences

Search of the Genbank with the blastp program using the castor bean PCPLD protein sequences as probe came up with a yeast DNA sequence (Genbank Accession# Z28256) that encodes a *S. cerevisiae* reading frame (ORF YKR031c) mapped to chromosome XI. This sequence contain several short stretches of amino acids homology to the plant PCPLD protein sequence. More recently, this yeast sequence has been identified to encode the SPO14 gene (Genbank Accession# L46807), a gene essential for yeast meiosis (Honigberg et al., *Genetics* 130:703–716, 1992). This yeast protein sequence was then used to search for homologous sequences in the Genbank database of expressed sequence tag (dbEST). Several short stretches of human cDNA sequences with homology to the plant PCPLD and the yeast SPO14 protein sequence were found. These cDNA sequences of interest were derived from single-run partial sequencing of random human cDNA clones carried out by either the WashU-Merck EST or the Genexpress-Genethon program. An example of a short stretch of amino acids sequence homology alignment among the plant, yeast and two overlapping human cDNA clones (genbank#R83570 and dbEST#261972) is shown, wherein castor bean PCPLD fragment is SEQ ID NO. 3, yeast is SEQ ID NO. 4, and R83570 is SEQ ID NO 5.

| Castor bean PCPLD | Q R S M D G A R D S E I A M G A Y Q P |
|---|---|
| Yeast SPO14 | E R S Q L G N R D S E V A I L I R D T |
| R83570/261972 | D R S L L G K R D S E L A V L I E D T |

The top row refers to the castor bean PCPLD sequence from amino acids 679–698, the middle row refers to the yeast SPO 14 sequence from amino acids 813–83 1, and the bottom row refers to a homologous translated sequence derived from human cDNA clone genbank#R83570 and dbEST#261972. Identical amino acids sequences among these three sequences are shown in block letters.

Accordingly, synthetic oligonucleotides 5'-GTATTCAATCCTGCATCGCCTTAA-3' (o.R83570.1) (SEQ ID NO. 6), 5'-GTCATCTGCGATGAGCACCTTGCTGTG-3' (o.R83570.1R) (SEQ ID NO. 7), were ordered (Life Technologies, Gaithersberg, Md.) based, respectively, on the putative coding sequence corresponding to nucleotides 44–67 and complement sequence corresponding to nucleotides 168–194 of the human cDNA clone genbank#R83570. o.R83570.1 was used in combination with the primer 5'-CTAGCTTATAATACGACTCA C-3'

(o.sport.1R) (SEQ ID NO. 8) corresponding to the vector sequence just downstream of the cDNA cloning region of the plasmid pCMV.SPORT (Life Technologies, Gaithersberg, Md.) to isolate the 3'-region of the human PCPLD cDNA from a human lung CDNA library (Life Technologies, Gaithersberg, Md.) using Expand™ long template PCR (Boehringer Mannheim, Indianapolis, Ind.). The PCR fragments generated were cleaved with Nco I and Xho I prior to subcloning into the Litmus28 vector (New England Biolab, Beverly, Mass.). DNA sequence analysis showed a cDNA clone with a 1,200 bp Nco I-Xho I insert contained a polyA tail at one end and a open reading frame with several stretches of homology corresponding to amino acids 766–862, 1228–1275 and 1338–1360 of the yeast SPO14 protein, suggesting that this c(DNA clone, pL28.NX, contained the C-terminal coding region of human PCPLD and its 3'-untranslated region.

o.R83570.1R was used in combination with the primer 5'-GACTCTAGCC TAGGCTTTTG C-3' (o.sport. 1) (SEQ ID NO. 9) corresponding to the vector sequence just upstream of the cDNA cloning region of the plasmid pCMV.SPORT (Life Technologies, Gaithersberg, Md.) to isolate the 5' -region of the human PCPLD cDNA from a human lung cDNA library (Life Technologies, Gaithersberg, Md.) using Expand™ long template PCR (Boehringer Mannheim, Indianapolis, Ind.). The PCR fragments generated were either cleaved with Sst I and Asp718 I or with Sst I alone prior to subcloning into the pBluescriptKS(-) vector (Stratagene, LaJolla, Calif.). DNA sequence analysis showed a cDNA clone with a 1,190 bp Sst I—Sst I insert contained a open reading frame with extensive homology to amino acids 401–780 of the yeast SP014 protein, suggesting that this cDNA clone, pKS.Sst, contained the central coding region of human PCPLD.

To isolate the 5'-region of the human PCPLD cDNA, a synthetic oligonucleotide 5'-CTCAGGACTCAACCACCAGT C-3' (o.pld3.2R, SEQ ID NO 10) was ordered (Life Technologies, Gaithersberg, Md.) based on the complement sequence corresponding to the region about 50 bp downstream of the Sst I site on the 5 '-side of the 1190 bp Sst I fragment. o.pld3.2R was used in combination with the primer 5'-GACTCTAGCC TAGGCTTTTG C-3' (o.sport.1) corresponding to the vector sequence just upstream of the cDNA cloning region of the plasmid pCMV.SPORT (Life Technologies, Gaithersberg, Md.) to isolate the 5'-region of the human PCPLD cDNA from a human lung cDNA library (Life Technologies, Gaithersberg, Md.) using Expand™ long template PCR (Boehringer Mannheim, Indianapolis, Ind.). The PCR fragments generated were cleaved with EcoR I prior to subcloning into the pBluescript(II)SK(-) vector (Stratagene, LaJolla, Calif.) between the EcoR I site and Sma I site. DNA sequence analysis showed a cDNA clone with a 1,240 bp insert contained an ATG near the 5'-end and a open reading frame with several major stretches of homology to amino acids 1–10, 153–262, and 328–410 of the yeast SPO14 protein, suggesting that this cDNA clone, pSK.R83.16, contained the N-terminal coding region of human PCPLD. It has recently been reported that the yeast SPO 14 gene did contain PCPLD activity (Engebrecht et al., *ASBMB Fall Symposium*, 1995), again suggesting that a human sequence with extensive homology to the yeast SPO 14 protein would have PCPLD activity.

To assemble the human PCPLD cDNA clone, the following fragments were isolated:

1) The 1197 bp Hind III-Sst I fragment from pSK.R83.16.
2) The 512 bp Sst I-Sfu I fragment from pKS.Sst.
3) The 660 bp Sfu I-Ban I fragment from pKS.Sst.
4) The 1129 bp Ban I-Xho I fragment from pL28.NX.

Fragments 1 and 2 were inserted via a three-part ligation into pLitmus28 (New England Biolab, Beverly, Mass.) cleaved with Sfu I and Hind III to generate pL28.HS. Fragments 3 and 4 were inserted via a three-part ligation into pLitmus28 cleaved with Sfu I and Xho I to generate pL28.SX. The 1700 bp Hind III-Sfu I fragment, derived from pL28.HS and the 1780 bp Sfu I-NotI fragment, derived from pL28.SX, were then inserted via a three-part ligation into the expression vector pCE2, cleaved with hind III and Not I to generate pCE2.PLD. pCE2.PLD is transfecting into various mammalian cells to assay for PCPLD activity using labeled-PC as a substrate (Ella et al., *Anal. Biochem.* 218: 136–142, 1994).

The plasmid pCE2 was derived from pREP7b (Leung et al., *Proc. Natl. Acad. Sci. USA*, 92:4813–4817, 1995) with the RSV promoter region replaced by the CMV enhancer and the elongation factor-1a (EF-1a) promoter and intron. The CMV enhancer came from a 380 bp Xba I-Sph I fragment produced by PCR from pCEP4 (Invitrogen, San Diego, Calif.) using the primers 5'-GGCTCTAGATATTAATAGTAATCAikTTAC-3' (SEQ ID NO. 11) and 5'-CCTCACGCATGCACCATGGTAATAGC-3' (SEQ ID NO 12). The EF-1a promoter and intron (Uetsuki et al., *J Biol. Chem.*, 264: 5791–5798, 1989) came from a 1200 bp Sph I-Asp718 I fragment produced by PCR from human genomic DNA using the primers 5'-GGTGCATGCGTGAGGCTCCGGTGC-3' (SEQ ID NO. 13)and 5'-GTAGTTTTCACGGTACCTGAAATGGAAG-3' (SEQ ID NO. 14). These 2 fragments were ligated into a Xba I/Asp718 I digested vector derived from pREP7b to generate pCE2

Nucleotide sequencing of the various human PCPLD cDNA inserts was performed. (SEQ ID NO. 1) shows the DNA sequence of the cDNA. insert of the human PCPLD isolated herein and the predicted amino acids sequence using the first ATG (nucleotide positions 66–68) from the 5'-end of the sequence for the start of translation. This open reading frame encodes a 933 amino acid polypeptide (SEQ ID NO. 1) and followed by a 3'-untranslated region of >550 bp. Although the putative initiation site for translation at nucleotide positions 66–68 fulfilled the requirement for an adequate initiation site (Kozak, *Critical Rev. Biochem. Mol. Biol.* 27:385–402, 1992). translation may still start further upstream of the sequence shown here, as there is no in frame stop codon preceding the 933 amino acid shown here.

The sequence of the 933 amino acid open reading frame in pCE2.PLD was used as the query sequence to search for homologous sequences in protein databases. Search of the database based on Genbank Release 91 from the National Center for Biotechnology Information (NCBI) using the blastp program showed that the protein encoded by pCE2.PLD was most homologous to the yeast SPO14 and the various plant PCPLDs.

Peptide Sequencing of Polypeptides

Purified polypeptides prepared by the methods described above can be sequenced using methods well known in the art, for example using a gas phase peptide sequencer (Applied Biosystems, Foster City, Calif.). Because the proteins of the present invention may be glycosylated, it is preferred that the carbohydrate groups are removed from the proteins prior to sequencing. This can be achieved by using glycosidase enzymes. Preferably, glycosidase F (Boehringer-Mannheim, Indianapolis, Ind.) is used. To determine as much of the polypeptide sequence as possible, it is preferred that the polypeptides of the present invention be cleaved into smaller fragments more suitable for gas-phase sequence analysis. This can be achieved by treatment of the polypeptides with selective peptidases, and in a particularly preferred embodiment, with endoproteinase lys-C (Boehringer). The fragments so produced can be separated by reversed-phase HPLC chromatography.

Production of Polypeptides

Once the entire coding sequence of the gene for the polypeptides has been determined, the gene can be inserted into an appropriate expression system. The gene can be expressed in any number of different recombinant DNA expression systems to generate large amounts of polypeptide. Included within the present invention are polypeptides having native glycosylation sequences, and deglycosylated or unglycosylated polypeptides prepared by the methods described below. Examples of expression systems known to the skilled practitioner in the art include bacteria such as *E. coli*, yeast such as *Pichia pastoris*, baculovirus, and mammalian expression systems such as in Cos or CHO cells. In a preferred embodiment, recombinant proteins are expressed in *E. coli* and in baculovirtis expression systems. The complete gene for the polypeptide can be expressed or, alternatively, fragments of the gene encoding antigenic determinants can be produced. In a first preferred embodiment, the gene sequence encoding the polypeptide is analyzed to detect putative transmembrane sequences. Such sequences are typically very hydrophobic and are readily detected by the use of standard sequence analysis software, such as MacDNASIS (Hitachi, San Bruno, Calif.). The presence of transmembrane sequences is often deleterious when a recombinant protein is synthesized in many expression systems, especially *E. coli*, as it leads to the production of insoluble aggregates which are difficult to renature into the native conformation of the polypeptide. Deletion of transmembrane sequences typically does not significantly alter the conformation of the remaining polypeptide structure. Moreover, transmembrane sequences, being by definition embedded within a membrane, are inaccessible as antigenic determinants to a host immune system. Antibodies to these sequences will not, therefore, provide immunity to the host and, hence, little is lost in terms of immunity by omitting such sequences from the recombinant polypeptides of the invention. Deletion of transmembrane-encoding sequences from the genes used for expression can be achieved by standard techniques. See Ausubel et al., infra, Chapter 8. For example, fortuitously-placed restriction enzyme sites can be used to excise the desired gene fragment, or the PCR can be used to amplify only the desired part of the gene.

Alternatively, computer sequence analysis is used to determine the location of the predicted major antigenic determinant epitopes of the recombinant polypeptide. Software capable of carrying out this analysis is readily available commercially, for example MacDNASIS (Hitachi, San Bruno, Calif.). The software typically uses standard algorithms such as the Kyte/Doolittle or Hopp/Woods methods for locating hydrophilic sequences which are characteristically found on the surface of polypeptides and are. therefore. likely to act as antigenic determinants. Once this analysis is made, polypeptides can be prepared which contain at least the essential features of the antigenic determinant. Genes encoding these determinants can be constructed and inserted into expression vectors by standard methods, for example, using PCR cloning methodology. Amino acid sequence variants of the polypeptides can be substitutional, insertional or deletion variants. Deletion variants lack one or more residues of the native polypeptide which are not essential for PCPLD activity, and are exemplified by the variants lacking a transmembrane sequence described above. Another common type of deletion variant is one lacking secretory signal sequences or signal sequences directing a polypeptide to bind to a particular part of a cell.

Substitutional variants typically contain the exchange of one amino acid for another at one or more sites within the protein, and are designed to modulate one or more properties of the polypeptides such as stability against proteolytic cleavage. Substitutions preferably are conservative, that is, one amino acid is replaced with one of similar shape and charge. Conservative substitutions are well known in the art and include, for example, the changes of: alanine to serine; arginine to lysine; asparigine to glutamirne or histidine; aspartate to glutamate; cysteine to serine; glutamine to asparigine; glutamate to aspartate; glycine to proline; histidine to asparigine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Insertional variants contain fusion proteins such as those used to allow rapid purification of the polypeptide and also can include hybrid polypeptides containing sequences from other proteins and polypeptides which are homologues of the inventive polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptides. These typically are smaller insertions than the fusion proteins described above and are introduced, for example, to disrupt a protease cleavage site.

The gene or gene fragment encoding the desired polypeptide can be inserted into an expression vector by standard subcloning techniques. In a preferred embodiment, an *E. Coli* expression vector is used which produces the recombinant protein as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6xHis system (Qiagen, Chatsworth, Calif.). Some of these systems produce recombinant polypeptides bearing only a small number of additional amino acids, which are unlikely to affect the PCPLD ability of the recombinant polypeptide. For example, both the FLAG system and the 6xHis system add only short sequences, both of which are known to be poorly antigenic and which do not adversely affect folding of the polypeptide to its native conformation. Other fusion systems produce proteins where it is desirable to excise the fusion partner from the desired protein. In a preferred embodiment, the fusion partner is linked to the recombinant polypeptide by a peptide sequence containing a specific recognition sequence for a protease. Examples of suitable sequences are those recognized by the Tobacco Etch Virus, protease (Life Technologies, Gaithersburg, Md.) or Factor Xa (New England Biolabs, Beverley, Mass.) or enterokinase (LaVallie et al., *J Biol. Chem.* 268:23311–17, 1993).

In another preferred embodiment, the expression system used is one driven by the baculovirus polyhedrin promoter. The gene encoding the polypeptide can be manipulated by standard techniques in order to facilitate cloning into the baculovirus vector. See Ausubel et al., supra. A preferred baculovirus vector is the pBlueBac vector (Invitrogen, Sorrento, Calif.). The vector carrying the gene for the polypeptide is transfected into *Spodoptera frugiperda* (Sf9) cells by standard protocols, and the cells are cultured and processed to produce the recombinant polypeptide. See Summers et al., *A Manual for Methods of Baculovirus Vectors and Insect Cell Culture Procedures*, Texas Agricultural Experimental Station.

Purification of Polypeptides.

In accordance with the invention, proteins are isolated from host cells, and tested for their ability to produce a desired biological response. Polypeptide extracts can be prepared from host cells by standard methods known to the art. See, for example, Harlow and Lane, *Antibodies, A Laboratory Manual*, Cold Spring Harbor Press, 1987 and *Current Protocols in Molecular Biology*, John Wiley & Sons 1995. In a preferred embodiment. host cells are extracted into a buffer, and the extracts separated into membrane and soluble fractions. Each fraction is tested for biological activity. Fractions which elicit a desired biological activity are then purified further to determine which components are responsible for the activity. At each step of the purification, fractions can be assayed for activity by the means described above. Purification of the active fractions can be carried out by methods known in the art. See, for example, *Protein Purification Methods—A Practical Approach*, Harris et al., Eds. (IRL Press, Oxford, 1989).

In a preferred embodiment, extracts prepared as above are purified by sequential size exclusion chromatography isoelectric focusing, HPLC size exclusion chromatography, and chromatography on an affinity column. Fractions which display PCPLD activity can be analyzed further by SDS-PAGE analysis to determine the approximate molecular mass of the active component. It is known that many naturally occurring polypeptides are glycosylated to varying degrees and, as a consequence, a single protein often appears as a pattern of bands of differing electrophoretic mobility on SDS-PAGE analysis. In such situations, it can be difficult to determine whether such a pattern is due to heterogeneity in glycosylation of a single amino acid chain or due to the presence of contaminating polypeptides. To distinguish between these two situations, the polypeptide fraction under study can be treated with a glycosidase to remove some or all the carbohydrate moieties from the protein. The SDS-PAGE analysis is repeated under both reducing and non-reducing conditions, and the resulting banding patterns compared. If the electrophoretic bands observed on the gel show similar or identical shifts in mobility after enzyme treatment, this is an indication that the electrophoretic heterogeneity observed in the purified protein fraction is due to variations in glycosylation. Conversely, if the electrophoretic mobilities differ significantly, this is evidence that contaminating polypeptides are present. In a preferred embodiment of the invention, the glycosidase is glycosidase F (Boehringer-Mannheim, Indianapolis, Ind.) and the peptidase is endoproteinase glu-C (Boehringer). The polypeptides may also be treated with a peptidase to cleave the protein into fragments for reversed phase HPLC mapping.

Some polypeptides have previously been purified from host cells and it is important therefore to exclude the possibility that biological activity in a particular fraction is due to the presence of these polypeptides. The presence of known polypeptides in a mixture can be detected by methods well known in the art, for instance, by Western blotting with an antiserum specific for the known polypeptide. In a preferred embodiment of the invention, previously identified polypeptides are removed from fractions containing antigenic activity by passage over affinity columns prepared using antibodies or antiserum specific for the known polypeptides.

The polypeptide expressed in any of a number of different recombinant DNA expression systems can be obtained in large amounts and tested for biological activity. The recombinant bacterial cells, for example *E. coli*, are grown in any of a number of suitable media, for example LB, and the expression of the recombinant polypeptide induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed. If the recombinant polypeptide is expressed in the inclusion, these can be washed in any of several solutions to remove some of the contaminating host proteins, then solubilized in solutions containing high concentrations of urea (e.g., 8M) or chaotropic agents such as guanidine hydrochloride in the presence of reducing agents such as β-mercaptoethanol or DTT (dithiothreitol).

At this stage it may be advantageous to incubate the polypeptide for several hours under conditions suitable for the polypeptide to undergo a refolding process into a conformation which more closely resembles that of the native polypeptide. Such conditions generally include low polypeptide (concentrations less than 500 mg/ml), low levels of reducing agent, concentrations of urea less than 2M and often the presence of reagents such as a mixture of reduced and oxidized glutathione which facilitate the interchange of disulphide bonds within the protein molecule. The refolding process can be monitored, for example, by SDS-PAGE or with antibodies which are specific for the native molecule. Following refolding, the polypeptide can then be purified further and separated from the refolding mixture by chromatography on any of several supports including ion exchange resins, gel permeation resins or on a variety of affinity columns.

More specifically, oligonucleotides and nucleic acids encoding a polypeptide of the invention can be used as hybridization probes, capable of recognizing and specifically binding to complementary nucleic acid sequences, providing thereby a means of detecting, identifying, locating and measuring complementary nucleic acid sequences in a biological sample.

Biological samples include, among a great many others, blood or blood serum, lymph, ascites fluid, urine, microorganism or tissue culture medium, cell extracts, or the like, derived from a biological source, or a solution containing chemically synthesized protein, or an extract or solution prepared from such biological-sourced fluid. It is further intended to include cells, tissue and other organic matter such as feces, food and plants.

An oligonucleotide containing a modified nucleotide of the invention can be used as a primer to initiate nucleic acid synthesis at locations in a DNA or RNA molecule comprising the sequence complementary to the inventive oligonucleotide sequence (SEQ ID NO. 1). The synthesized nucleic acid strand would have incorporated, at its 5' terminus, the oligonucleotide primer bearing the inventive sequence and would, therefore, be detectable by exploitation of the characteristics of the detectable label. Two such primers, specific for different nucleotide sequences on complementary strands of dsDNA, can be used in the polymerase chain reaction (PCR) to synthesize and amplify the amount of a nucleotide sequence. The detectable label present on the primers will facilitate the identification of desired PCR products. PCR, combined with techniques for preparing complementary DNA (cDNA) can be used to amplify various RNAs, with oligonucleotide primers again serving both to provide points for initiation of synthesis in the cDNA duplex flanking the desired sequence and to identify the desired product. Primers labeled with the invention may also be utilized for enzymatic nucleic acid sequencing by the dideoxy chain-termination technique.

Alternatively, expression vectors are introduced into Brassica tissues using a direct gene transfer method such as microprojectile-mediated delivery, DNA injection, electroporation, and the like. See, for example, Klein et al., *Biotechnology* 10:268, 1992.

PCR Background Information

Polymerase chain reaction (PCR) technology is employed in a growing variety of ways, including preparation of cDNAs and constructing cDNA libraries. An early use of PCR to generate a cDNA library was reported by Belyavsky et al., *Nucleic Acids Res.* 7:2919–32, 1989. The Belyavsky method utilized oligo (dT) as a primer for reverse transcriptase reaction, followed by poly (dG) tailing via the action of terminal deoxynucleotidyl transferase (TdT). The resulting dg-tailed cDNAs were subsequently amplified with poly (dT) and poly (dC) primers. The cDNA pool obtained was cloned into a vector for subsequent cDNA screening. Since an oligo (dT) primer can anneal at any position of the poly(A) tail of a (+) strand of cDNA, and an oligo (dC) primer can anneal at any position of the poly(G) tail of a (−) strand of cDNA, the amplified cDNAs generated by the Belyavsky method often have varying lengths. Accordingly, these products cannot be analyzed directly, and instead require subcloning and screening of a cDNA library, a time-consuming technique. Furthermore, the use of primers containing homopolymers on the 3' end typically yields a high background of non-specific product.

A technique for rapid amplification of cDNA ends (RACE) was in Frohman et al., *Proc. Nat'l. Acad. Sci. USA* 85:8998–9002, 1988, and Frohman, *PCR Protocols, A Guide to Methods and Applications*, 28–38 (Academic Press 1990). The RACE protocol produces specific cDNAs by using PCR to amplify the region between a single point on a transcript and the 3' or the 5' ends. One requires knowledge of the sequence of an internal portion of the transcript, however, in order to design a primer for use in conjunction with either the polyT or polyG primers to amplify the ends. This protocol yields specific cDNAs produces only, not whole libraries.

A modification to the RACE protocol introduced by Borson et al., *PCR Methods and Applications* 2:144–48, 1992, entails the use of a "lock-docking oligo (dT)." The locking mechanism involves extending the poly dT primer, by either one nucleotide (A, C or G) or by two nucleotides (also A, C or G) and yet one more of the four possible nucleotides, at the 3'-end of the primer. This "locks" the primer to the beginning of the poly dT tail, either the natural dT or a poly dT tail attached to the first strand cDNA 3'-end, by use of TdT, resulting in the synthesis of cDNA's of discrete lengths. Subcloning and screening of subclone library is not necessary before analysis, which can speed up the inquiry. Like the RACE protocol, however, Borson's protocol uses a gene-specific internal primer and, hence, produces only specific cDNAs, not whole libraries.

Approaches are described in the literature to identify mRNA expressed differentially, either in only some cell types, or at certain times of a biological process, or during infection by a parasite or a virus, etc. Those studies generally employ subtractive hybridization to reveal the differentially expressed mRNA(s). Liang and colleagues have used the anchored-end technique to look for specific differences in mRNA populations. Liang et al., *Nucleic Acids Res.* 21:3269–75, 1993. The Liang method, called "differential display," employs a decanucleotide of arbitrary sequence as a primer for PCR, internal to the mRNA, and a polyTMN primer on the 3'-end of mRNAs; "M" in this context is randomly G, C or A, but N is chosen as one of the four possible nucleotides. When such sets of primers are employed, patterns of mRNAs can be visualized, upon polyacrylamide gel electrophoresis of the PCR product, and the comparison of such patterns produced by mRNAs from two sources reveal the differentially expressed mRNAs.

The differential display method can indicate the individual, differently expressed mRNA's, but cannot constitute a complete library of such mRNA's. As a further consequence of having one primer of an arbitrary sequence, and therefore probably not having an exact match, low copy number mRNAs may not be picked up by this method. Finally, the cDNA candidates identified would still require recovery from the gel and subcloning, if the individual cDNA is desired for further analysis.

Lisitsyn et al., *Science* 259:946–51, 1993, have described a representational differences analysis (RDA) which uses subtractive hybridization and PCR technology to define the differences between two genomes. Like other subtractive hybridization protocols, in RDA there are defined two sets of DNAs, the "tester" DNA and the "driver" DNA. According to the RDA protocol, the DNA of the two genomes to be compared are digested by restriction endonucleases, and a dephoshorylated double-stranded oligonucleotide adapter is ligated. After denaturation and hybridization of driver and tester DNA, oligonucleotides from the adapters covalently linked to tester DNA were used to amplify unique DNA sequences of tester library. The adapters are partially double-stranded DNAs made by partially complementary oligos, where the single-stranded sequence at one end of the double stranded adapter is complementary to the single-strand tail of the digested genomic DNA. The combined use of (i) restriction enzyme, digested DNA as PCR substrate and (ii) the preferential amplification of shorter substrates results in a population of fairly short, amplified DNA molecules. The adapters then are removed by cleavage with the restriction enzymes used originally to digest the DNA. To the tester DNA, new adapters with novel sequences are ligated, the tester and driver DNA are mixed, the DNA strands are separated by heating ("melting"), and the DNA's are cooled to allow for reannealing. PCR is performed with primers complementary to the adapters on tester DNA. thereby amplifying only target DNA, i.e., only DNA unique to the tester DNA. By restriction enzyme digestion of the adapters from the amplified DNA and ligation of additional, novel adapters, followed by PCR, the target DNA is amplified to become the dominant fraction.

The RDA procedure does not use any physical method of separation between the tester and driver DNA which, if used, would allow enhanced purification of target DNA. The method is used only to identify differences between genomes and was not used to identify differential cDNA expression.

Expression vectors that are suitable for production of PCPLD polypeptide typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. PCPLD polypeptide of the present invention preferably is expressed in eukaryotic cells, such as mammalian, insect and yeast cells. Mammalian cells are especially preferred eukaryotic hosts because mammalian cells provide suitable post-translational modifications such as glycosylation. Examples of mammalian host cells include Chinese hamster ovary cells (CHO-K1; ATCC CCL61), rat pituitary cells ($GH_1$; ATCC CCL82), HeLa S3 cells (ATCC CCL2.2), rat hepatoma cells (H-4-II-E; ATCC CRL1548) SV40-transformed monkey kidney cells (COS-1; ATCC CRL 1650) and murine embryonic cells (NIH-3T3; ATCC CRL 1658). For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273,1982); the TK promoter of Herpes virus (McKnight, Cell 31: 355, 1982); the SV40 early promoter (Benoist et al., *Nature* 290:304, 1981); the Rous sarcoma virus promoter (Gorman et al., *Proc. Nat'l. Acad. Sci. USA* 79:6777, 1982); and the cytomegalovirus promoter (Foecking et al., *Gene* 45:101, 1980). Alternatively, a prokaryotic promoter, such as the bacteriophage T3 RNA polymerase promoter, can be used to control fusion gene expression if the prokaryotic promoter is regulated by a eukaryotic promoter. Zhou et al., *Mol. Cell. Biol.* 10:4529, 1990; Kaufman et al., *Nucl. Acids Res.* 19:4485, 1991.

An expression vector can be introduced into host cells using a variety of techniques including calcium phosphate transfection, liposome-mediated transfection, electroporation, and the like. Preferably, transfected cells are selected and propagated wherein the expression vector is stably integrated in the host cell genome to produce stable transformants. Techniques for introducing vectors into eukaryotic cells and techniques for selecting stable transformants using a dominant selectable marker are described, for example, by Ausubel and by Murray (ed.), *Gene Transfer and Expression Protocols* (Humana Press 1991).

DNA molecules encoding the human PCPLD gene can be used to detect the level of PCPLD gene expression in tissue samples. Such a detection method can be used, for example, to compare the amount of PCPLD RNA in a sample obtained from normal tissue and in a sample isolated from methotrexate-resistant tumor tissue. The presence of relatively low levels of PCPLD RNA in the tumor sample would indicate that methotrexate resistance is due, at least in part, to underexpression of the PCPLD gene. This result also would indicate that treatment of a mammal having such a tumor with methotrexate should be augmented by PCPLD gene therapy.

In testing a tissue sample for PCPLD RNA using a nucleic acid hybridization assay, RNA can be isolated from tissue by sectioning on a cryostat and lysing the sections with a detergent such as SDS and a chelating agent such as EDTA, optionally with overnight digestion with proteinase K. Such tissue is obtained by biopsy. A preferred quantity of tissue is in the range of 1–10 milligrams. Protein is removed by phenol and chloroform extractions, and nucleic acids are precipitated with ethanol. RNA is isolated by chromatography on an oligo dT column and then eluted from the column. Further fractionation also can be carried out according to methods well known to those of ordinary skill in the art.

A number of techniques for molecular hybridization are used for the detection of DNA or RNA sequences in tissues. When large amounts of tissue are available, analysis of hybridization kinetics provides the opportunity to accurately quantitate the amount of DNA or RNA present, as well as to distinguish sequences that are closely related but not identical to the probe. Reactions are run under conditions of hybridization (Tm—25° C.) in which the rate of reassociation of the probe is optimal. Wetmur et al., *J. Mol. Biol.* 31:349, 1968. The kinetics of the reaction are second order when the sequences in the tissue are identical to those of the probe; however, the reaction exhibits complex kinetics when probe sequences have partial homology to those in the tissue. Sharp et al., *J. Mol. Biol.* 86:709, 1974.

The concentration of probe to cellular RNA is determined by the sensitivity desired. To detect one transcript per cell would require about 100 pg of probe per mg of total cellular DNA or RNA. The nucleic acids are mixed, denatured, brought to the appropriate salt concentration and temperature, and allowed to hybridize for various periods of time. The rate of reassociation can be determined by quantitating the amount of probe hybridized either by hydroxyapatite chromatography (Britten et al., *Science* 161:529, 1968) or by S1 nuclease digestion (Sutton, *Biochim. Biophys. Acta* 240:522, 1971).

A more flexible method of hybridization is the northern blot technique. The particular hybridization technique is not essential to the invention, and any technique commonly used in the art being within the scope of the present invention. Typical probe technology is described in U.S. Pat. No. 4,358,535 to Falkow et al., incorporated by reference herein. For example, hybridization can be carried out in a solution containing 6× SSC (10× SSC: 1.5M sodium chloride, 0.15M sodium citrate, pH 7.0), 5× Denhardt's (1× Denhardt's: 0.2% bovine serum albumin, 0.2% polyvinylpyrrolidone, 0.02% Ficoll 400), 10 mM EDTA, 0.5% SDS and about $10^7$ cpm of nick-translated DNA for 16 hours at 65° C.

The hybridization assays of the present invention are particularly well suited for preparation and commercialization in kit form, the kit comprising a carrier means compartmentalized to receive one or more container means (vial, test tube, etc.) in close confinement, with each container means comprising one of the separate elements to be used in hybridization assay. For example, there may be a container means containing PCPLD DNA molecules suitable for labeling by "nick translation," or containing labeled PCPLD DNA or labeled PCPLD RNA molecules. Further container means may contain standard solutions for nick translation of DNA comprising DNA polymerase I/DNase I and unlabeled deoxyribonucleotides.

Antibodies to human PCPLD protein can be obtained using the product of an PCPLD expression vector as an antigen. The preparation of polyclonal antibodies is well-known to those of skill in the art. See, for example, Green et al., "Production of Polyclonal Antisera," in *Immunochemical Protocols* (Manson, ed.), pages 1–5 (Humana Press 1992). Alternatively, an PCPLD antibody of the present invention may be derived from a rodent monoclonal antibody (MAb). Rodent monoclonal antibodies to specific antigens may be obtained by methods known to those skilled in the art. See, for example, Kohler and Milstein, Nature 256:495, 1975, and Coligan et al. (eds.), Current Protocols in Immunology, 1:2.5.1–2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridonia cultures by a variety of well-established techniques. Such isolation techniques include affinity chromatography with Protein-A Sepharose, size-exclusion chromatography, and ion-exchange chromatography. See, for example, Coligan at pages 2.7.1–2.7.12 and pages 2.9.1–2.9.3. Also, see Baines et al., "Purification of Immunoglobulin G (IgG)," in Methods in Molecular Biology, 10:79–104 Humana Press, Inc. 1992. A PCPLD antibody of the present invention may also be derived from a subhuman primate antibody. General techniques for raising therapeutically useful antibodies in baboons may be found, for example, in Goldenberg et al., international patent publication No. WO 91/11465 (1991), and in Losman et al., Int. J. Cancer 46:310, 1990.

Alternatively, a therapeutically useful PCPLD antibody may be derived from a "humanized" monoclonal antibody. Humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example. by the publication of Orlandi et al., Proc. Nat'l. Acad. Sci. USA 86:3833, 1989. Techniques for producing humanized MAbs are described, for example, by Jones et al., Nature 321:522, 1986, Riechmann et al., Nature 332:323, 1988, Verhoeyen et al., Science 239:1534, 1988, Carter et al., Proc. Nat'l Acad. Sci. USA 89:4285, 1992, Sandhu, Crit. Rev. Biotech. 12:437, 1992, and Singer et al., J Immun. 150:2844, 1993, each of which is hereby incorporated by reference.

As an alternative, a PCPLD antibody of the present invention may be derived from human antibody fragments isolated from a combinatorial immunoglobulin library. See, for example, Barbas et al., METHODS; A Companion to Methods in Enzymology 2:119 1991, and Winter et al., Ann. Rev. Immunol. 12:433, 1994, which are incorporated by reference. Cloning and expression vectors that are useful for producing a human immunoglobulin phage library can be obtained, for example, from STRATAGENE Cloning Systems (La Jolla, Calif.). In addition, a PCPLD antibody of the present invention may be derived from a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13, 1994; Lonberg et al., Nature 368:856, 1994, and Taylor et al., Int. Immun. 6:579, 1994.

The invention, illustrated by the following examples, should not be deemed as limited in any way by the following representative examples.

EXAMPLE 1

This example illustrates that the recombinant human PCPLD enzyme is useful in developing an assay for screening assay compounds that modulate PCPLD activity. FIG. 1 shows an example of a screening assay for PCPLD activity in cell extracts based on a fluorecent asssay (Ella, et al., Anal. Biochem. 218: 136–142, 1994) with the major exception that, instead of using the substrate BPC (Molecular Probes, Eugene, Oreg.), we used a synthetic phosphatidylcholine (PC) substrate with a fluorescent NBD moiety incorporated into the end of the acyl-chain at the SN1 position of PC (NBD-PC). BPC contains an ether linkage at the sn-1 position, while NBD-PC contains an acyl linkage at the sn-1 position. Having an acyl linkage at the sn1position provides the additional opportunity to examine PLA1 activity along with other PC-hydrolysing phospholipases such as PCPLD, PCPLC, and PLA2 at the same time.

The assay for PCPLD uses the transphosphatidyiation (Saito, et al., Arch. Biochem. Biophys. 169: 318–323, 1975) reaction as a means of defining PCPLD activity. This reaction occurs when PCPLD hydrolyses PC into PA and choline in presence of a primary alcohol, such as butanol, where PA will be converted to phosphatidylbutanol (PBt). Pbt is more resistant to hydrolysis by enzymes such as PA phosphohydrolase (PAPh) and can be easily separated from PC and other products by thin layer chromatography. In this particular example, cell lysate was prepared from Sf9 cells that have been transfected with Baculoviral constructs expressing PCPLD and another human isoform (Hammond, et al., J. Biol. Chem. 270: 29640–29643, 1995), hPLD1.6. The samples were then incubated with NBD-PC for 30 min at 30° before loading onto TLC plates. Lane 1 refers to NBD-PC digested with cabbage PCPLD (Sigma, St. Louis, Mo.) for the generation of certain lipid standards. Lanes 2 to 4 refer to NBD-PC treated with cell lysates that have been transfected with Baculoviral constructs expressing hPCPLD, hPLD1, and β-glucuronidase as a negative control. Lane 5 refers to NBD-PC treated with B. cereus PCPLC (Sigma, St. Louis, Mo.) for the generation of NBD-DAG standard. Lane 6 refers to the starting substrate, NBD-PC, by itself. FIG. 1 shows the activity level of Sf9 cells transfected with hPLD1 and hPCPLD, as evidenced by the fluorescent intensity of the products corresponding to NBD-PBt and NBD-PA on the TLC plate.

EXAMPLE 2

This example illustrates how recombinant hPLD1, as representative of other PLD isoforms, would be used in a screening assay for compounds that modulate PCPLD activity. The results of this assay are shown in FIG. 2.

Figure 2:
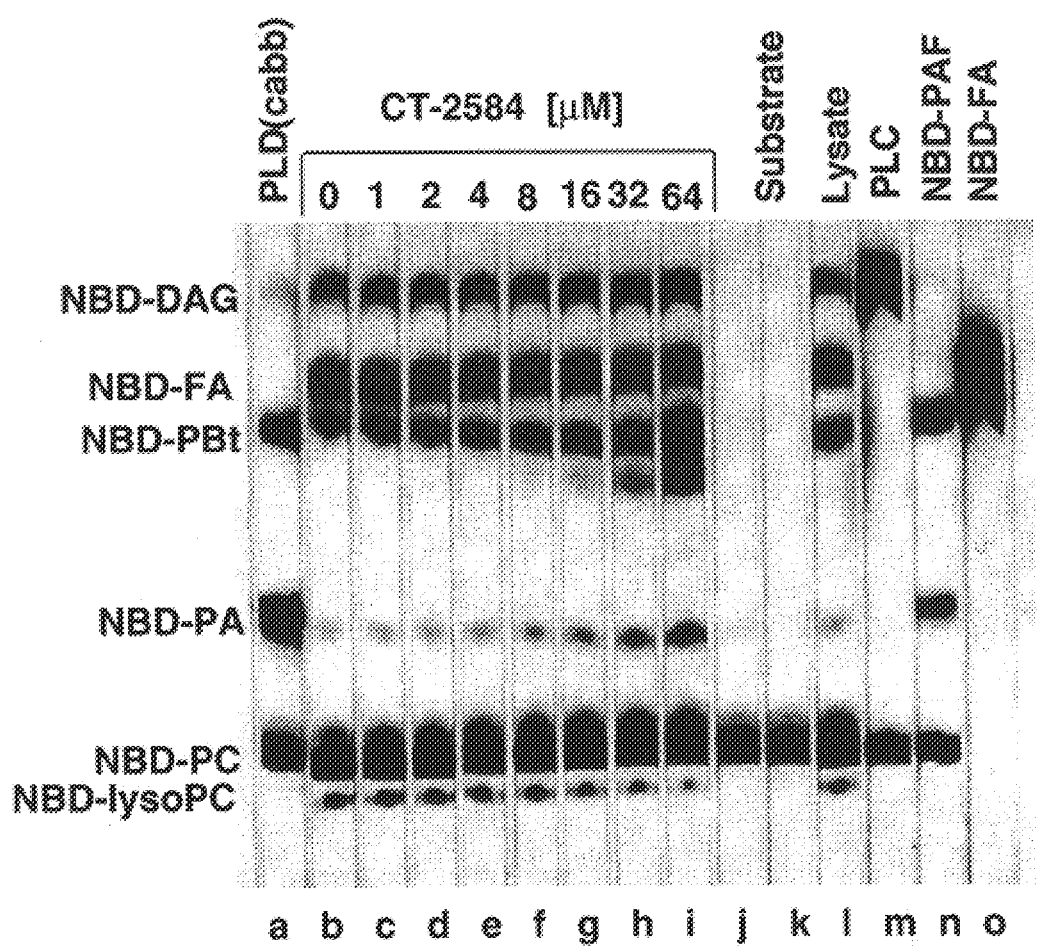
FIG. 2 shows the effect of CT-2584 on PCPLD activity in insect cell extracts transfected with a Baculoviral construct expressing hPLD1.

FIG. 2 illustrates an example of CT-2584 on recombinant hPLD1 activity. In this particular example, cell lysate was prepared from insect cell extracts transfected with Baculoviral vector expressing hPLD1. The samples were incubated with NBD-PC along with various concentrations of an anti-tumor compound, CT-2485 for 30 min before loading onto TLC plates (Lanes 2 to 7). Lane 1 refers to NBD-PC, a PC with a NBD-group at the SN1 acyl chain. Lane 8 refers to cell extract treated with the vehicle control for CT-2584. Lane 9 refers to cell extracts transfected with Baculoviral vector expressing the control β-glucuronidase reporter gene. Lane 10 refers to NBD-PC digested with cabbage PCPLD (Sigma, St. Louis, Mo.) for the generation of certain lipid standards. Lane 11 refers to NBD-PC treated with B. cereus PCPLC (Sigma, St. Louis, Mo.) for the generation of NBD-DAG standard. FIG. 2 shows that increasing concentration of CT-2584 led to increase in activity of PCPLD and PCPLC, as evidenced by the increase in flourescent intensity of the products corresponding to NBD-Pa-Bt, NBD-LPA-Bt, and NBD-PA on the TLC plate. On the other hand, CT-2584 has little effect on PLA1 and PLA2 activity, as evidenced by the even flourescent intensity of the products corresponding to NBD-free fatty acid (NBD-FIFA) and NBD-lysophosphatidic acid (NBD-LPC) across the TLC plate. This type of assays may be useful to screen for agonists and antagonists of PCPLD, as PCPLD has been found to be activated in response to treatment of cells with various hormones and growth factors (Exton, *Biochim Biophys Acta* 1212: 26–42, 1994).

---

We claim:

1. An isolated and purified nucleic acid sequence coding an expression for a biologically active human phosphatidyl-chloline phospholipase D enzyme selected from the group consisting of:

(a) a DNA sequence set forth in SEQ ID NO. 1 and biologically active fragments thereof;

(b) a cDNA sequence which, due to the degeneracy of the genetic code, encodes a polypeptide of SEQ ID NO. 1 and biologically active fragments thereof; and (c) a cDNA sequence capable of hybridizing under high stringency conditions to a cDNA sequence encoding a polypeptide having PCPLD bioloical activity.

* * * * *